(12) United States Patent
Geng et al.

(10) Patent No.: US 12,241,886 B2
(45) Date of Patent: Mar. 4, 2025

(54) TRANSMEMBRANE NANOPORE WITH NUCLEIC ACID UNWINDING FUNCTION AND ITS CONSTRUCTION METHODS AND APPLICATIONS

(71) Applicant: Guangzhou Kongque Gene Technology Co. LTD., Guangzhou (CN)

(72) Inventors: Jia Geng, Chengdu (CN); Yuquan Wei, Chengdu (CN)

(73) Assignee: Guangzhou Kongque Gene Technology Co. LTD., Guangzhou (CN)

( * ) Notice: Subject to any disclaimer, the term of this patent is extended or adjusted under 35 U.S.C. 154(b) by 624 days.

(21) Appl. No.: 16/480,209

(22) PCT Filed: Jan. 23, 2018

(86) PCT No.: PCT/CN2018/073716
§ 371 (c)(1),
(2) Date: Jul. 23, 2019

(87) PCT Pub. No.: WO2018/137592
PCT Pub. Date: Aug. 2, 2018

(65) Prior Publication Data
US 2019/0383790 A1 Dec. 19, 2019

(30) Foreign Application Priority Data
Jan. 24, 2017 (CN) .......................... 201710060033.9

(51) Int. Cl.
| | | |
|---|---|---|
| C12N 9/14 | (2006.01) | |
| A61K 9/70 | (2006.01) | |
| A61K 47/42 | (2017.01) | |
| C07K 14/00 | (2006.01) | |
| C12N 15/37 | (2006.01) | |
| C12N 15/55 | (2006.01) | |
| C12Q 1/6869 | (2018.01) | |
| G01N 33/487 | (2006.01) | |
| B82Y 5/00 | (2011.01) | |

(52) U.S. Cl.
CPC ..... G01N 33/48721 (2013.01); A61K 9/7007 (2013.01); A61K 47/42 (2013.01); C07K 14/00 (2013.01); C12N 9/14 (2013.01); C12Q 1/6869 (2013.01); B82Y 5/00 (2013.01); C12N 2710/20022 (2013.01); C12Q 2565/631 (2013.01); C12Y 306/04012 (2013.01); G01N 2333/914 (2013.01)

(58) Field of Classification Search
None
See application file for complete search history.

(56) References Cited

FOREIGN PATENT DOCUMENTS

| | | |
|---|---|---|
| CN | 102902895 A | 1/2013 |
| CN | 104710519 A | 6/2015 |
| EP | 2768977 B1 | 9/2015 |

OTHER PUBLICATIONS

UniProt Database Accession No. P03116, Nov. 2016, 5 pages (Year: 2016).*
Singh et al., Curr. Protein Pept. Sci. 18:1-11, 2017 (Year: 2017).*
Zhang et al., Structure 26:1474-1485, 2018 (Year: 2018).*
Sanders et al., Nucleic Acids Res. 35:6451-6457, 2007 (Year: 2007).*
Enemark et al., Nature 442:270-275, 2006 (Year: 2006).*
Rangasamy et al., J. Biol. Chem. 275:30487-30495, 2000 (Year: 2000).*
Schultz et al., Proteins Structure and Function, pp. 521-528, Plenum Press, New York, 1987 (Year: 1987).*
Airaksinen et al., Nucleic Acids Res. 26:576-581, 1998 (Year: 1998).*
UniProt Database Accession No. K4PCQ2, Sep. 2016, 2 pages (Year: 2016).*
Yang et al., Proc. Natl. Acad. Sci. 90:5086-5090, 1993 (Year: 1993).*
UniProt Database Accession No. A0A0E3SY48, Sep. 2016, 3 pages (Year: 2016).*
UniProt Database Accession No. A0A0F7GFM9, Sep. 2016, 2 pages (Year: 2016).*
Derrington et al. (2010). Nanopore DNA sequencing with MspA. PNAS, 107(37), 16060-16065.
Derrington et al. (2015). Subangstrom single-molecule measurements of motor proteins using a nanopore. Nature Biotechnology, 1-4.
Laszlo et al. (2014). Decoding long nanopore sequencing reads of natural DNA. Nature Biotechnology, 1-6.
Manrao et al. (2012). Reading DNA at single-nucleotide resolution with a mutant MspA nanopore and phi29 DNA polymerase. Nature Biotechnology, 30(4), 349-354.
NP_056739.1 E1 Protein [Bovine Papillomavirus-1], NCBI, (2017), retrieved from https://www.ncbi.nlm.nih.gov/protein/YP_009389516.1.

(Continued)

Primary Examiner — David Steadman
(74) Attorney, Agent, or Firm — JCIP; Joseph G. Chu

(57) ABSTRACT

This invention belongs to the field of biotechnology, in particular to a mutant double-strand DNA (dsDNA) helicase protein nanopore derived from bovine papillomavirus and its application. The technical problem to be solved by this invention is to overcome the deficiency that the existing small-diameter protein nanopore requires an external strength or component to transport dsDNA. The technical scheme in this invention to solve the above deficiency is to provide a truncated E1-1 (306-577) protein, an E1-2 (306-605) protein and its variant derived from bovine papillomavirus double-stranded DNA helicase protein, as well as a variant of its homologous protein which is used for preparing membrane containing conductive channel, providing a new and effective choice for this field.

13 Claims, 14 Drawing Sheets

Specification includes a Sequence Listing.

(56) References Cited

OTHER PUBLICATIONS

NP_056739.1 E1 Protein [Deltapapillomavirus 4], NCBI, (2000) retrieved from https://www.ncbi.nlm.nih.gov/protein/NP_056739.1.

* cited by examiner

```
                        SEQUENCE LISTING

<160> NUMBER OF SEQ ID NOS: 27

<210> SEQ ID NO 1
<211> LENGTH: 300
<212> TYPE: PRT
<213> ORGANISM: Artificial Sequence
<220> FEATURE:
<223> OTHER INFORMATION: The amino acid sequence of truncated E1-2
      (306-605)

<400> SEQUENCE: 1

Leu Gln Thr Glu Lys Phe Asp Phe Gly Thr Met Val Gln Trp Ala Tyr
1               5                   10                  15

Asp His Lys Tyr Ala Glu Glu Ser Lys Ile Ala Tyr Glu Tyr Ala Leu
            20                  25                  30

Ala Ala Gly Ser Asp Ser Asn Ala Arg Ala Phe Leu Ala Thr Asn Ser
        35                  40                  45

Gln Ala Lys His Val Lys Asp Cys Ala Thr Met Val Arg His Tyr Leu
    50                  55                  60

Arg Ala Glu Thr Gln Ala Leu Ser Met Pro Ala Tyr Ile Lys Ala Arg
65                  70                  75                  80

Cys Lys Leu Ala Thr Gly Glu Gly Ser Trp Lys Ser Ile Leu Thr Phe
                85                  90                  95

Phe Asn Tyr Gln Asn Ile Glu Leu Ile Thr Phe Ile Asn Ala Leu Lys
            100                 105                 110

Leu Trp Leu Lys Gly Ile Pro Lys Lys Asn Cys Leu Ala Phe Ile Gly
        115                 120                 125

Pro Pro Asn Thr Gly Lys Ser Met Leu Cys Asn Ser Leu Ile His Phe
130                 135                 140

Leu Gly Gly Ser Val Leu Ser Phe Ala Asn His Lys Ser His Phe Trp
145                 150                 155                 160

Leu Ala Ser Leu Ala Asp Thr Arg Ala Ala Leu Val Asp Asp Ala Thr
                165                 170                 175

His Ala Cys Trp Arg Tyr Phe Asp Thr Tyr Leu Arg Asn Ala Leu Asp
            180                 185                 190

Gly Tyr Pro Val Ser Ile Asp Arg Lys His Lys Ala Ala Val Gln Ile
        195                 200                 205

Lys Ala Pro Pro Leu Leu Val Thr Ser Asn Ile Asp Val Gln Ala Glu
    210                 215                 220

Asp Arg Tyr Leu Tyr Leu His Ser Arg Val Gln Thr Phe Arg Phe Glu
225                 230                 235                 240

Gln Pro Cys Thr Asp Glu Ser Gly Glu Gln Pro Phe Asn Ile Thr Asp
                245                 250                 255

Ala Asp Trp Lys Ser Phe Phe Val Arg Leu Trp Gly Arg Leu Asp Leu
            260                 265                 270

Ile Asp Glu Glu Glu Asp Ser Glu Asp Gly Asp Ser Met Arg Thr
        275                 280                 285

Phe Thr Cys Ser Ala Arg Asn Thr Asn Ala Val Asp
    290                 295                 300
```

<210> SEQ ID NO 2
<211> LENGTH: 903
<212> TYPE: DNA
<213> ORGANISM: Artificial Sequence
<220> FEATURE:
<223> OTHER INFORMATION: The encoding DNA sequence of truncated E1-2 (306-605)

<400> SEQUENCE: 2

```
ttgcagaccg agaaattcga cttcggaact atggtgcaat gggcctatga tcacaaatat      60
gctgaagagt ctaaaatagc ctatgaatat gctttggctg caggatctga tagcaatgca     120
cgggcttttt tagcaactaa cagccaagct aagcatgtga aggactgtgc aactatggta     180
agacactatc taagagctga aacacaagca ttaagcatgc ctgcatatat aaagctagg      240
tgcaagctgg caactgggga aggaagctgg aagtctattc aactttttt taattatcag     300
aatattgaat taattacctt tattaatgct ttaaagctct ggctaaaagg aattccaaaa     360
aaaaactgtt tagcatttat tggccctcca aacacaggca agtctatgct ctgcaactca     420
ttaattcatt ttttgggtgg tagtgtttta tcttttgcca accataaaag tcacttttgg     480
cttgcttccc tagcagatac tagagctgct ttagtagatg atgctactca tgcttgctgg     540
aggtactttg acacatacct cagaaatgca ttggatggct accctgtcag tattgataga     600
aaacacaaag cagcggttca aattaaagct ccacccctcc tggtaaccag taatattgat     660
gtgcaggcag aggacagata tttgtacttg catagtcggg tgcaaacctt tcgctttgag     720
cagccatgca cagatgaatc gggtgagcaa cctttaata ttactgatgc agattggaaa      780
tctttttttg taaggttatg ggggcgttta gacctgattg acgaggagga ggatagtgaa     840
gaggatggag acagcatgcg aacgtttaca tgtagcgcaa gaaacacaaa tgcagttgat     900
tga                                                                   903
```

<210> SEQ ID NO 3
<211> LENGTH: 272
<212> TYPE: PRT
<213> ORGANISM: Artificial Sequence
<220> FEATURE:
<223> OTHER INFORMATION: The amino acid sequence of truncated E1-1 (306-577)

<400> SEQUENCE: 3

```
Leu Gln Thr Glu Lys Phe Asp Phe Gly Thr Met Val Gln Trp Ala Tyr
 1               5                  10                  15

Asp His Lys Tyr Ala Glu Glu Ser Lys Ile Ala Tyr Glu Tyr Ala Leu
            20                  25                  30

Ala Ala Gly Ser Asp Ser Asn Ala Arg Ala Phe Leu Ala Thr Asn Ser
        35                  40                  45

Gln Ala Lys His Val Lys Asp Cys Ala Thr Met Val Arg His Tyr Leu
    50                  55                  60

Arg Ala Glu Thr Gln Ala Leu Ser Met Pro Ala Tyr Ile Lys Ala Arg
65                  70                  75                  80

Cys Lys Leu Ala Thr Gly Glu Gly Ser Trp Lys Ser Ile Leu Thr Phe
                85                  90                  95

Phe Asn Tyr Gln Asn Ile Glu Leu Ile Thr Phe Ile Asn Ala Leu Lys
            100                 105                 110

Leu Trp Leu Lys Gly Ile Pro Lys Lys Asn Cys Leu Ala Phe Ile Gly
        115                 120                 125

Pro Pro Asn Thr Gly Lys Ser Met Leu Cys Asn Ser Leu Ile His Phe
```

Leu Gly Gly Ser Val Leu Ser Phe Ala Asn His Lys Ser His Phe Trp
145                 150                 155                 160

Leu Ala Ser Leu Ala Asp Thr Arg Ala Ala Leu Val Asp Asp Ala Thr
                165                 170                 175

His Ala Cys Trp Arg Tyr Phe Asp Thr Tyr Leu Arg Asn Ala Leu Asp
            180                 185                 190

Gly Tyr Pro Val Ser Ile Asp Arg Lys His Lys Ala Ala Val Gln Ile
        195                 200                 205

Lys Ala Pro Pro Leu Leu Val Thr Ser Asn Ile Asp Val Gln Ala Glu
    210                 215                 220

Asp Arg Tyr Leu Tyr Leu His Ser Arg Val Gln Thr Phe Arg Phe Glu
225                 230                 235                 240

Gln Pro Cys Thr Asp Glu Ser Gly Glu Gln Pro Phe Asn Ile Thr Asp
                245                 250                 255

Ala Asp Trp Lys Ser Phe Phe Val Arg Leu Trp Gly Arg Leu Asp Leu
            260                 265                 270

<210> SEQ ID NO 4
<211> LENGTH: 816
<212> TYPE: DNA
<213> ORGANISM: Artificial Sequence
<220> FEATURE:
<223> OTHER INFORMATION: The encoding DNA sequence of truncated E1-1
      (306-577)

<400> SEQUENCE: 4
ttgcagaccg agaaattcga cttcggaact atggtgcaat gggcctatga tcacaaatat     60
gctgaggagt ctaaaatagc ctatgaatat gctttggctg caggatctga tagcaatgca    120
cgggcttttt tagcaactaa cagccaagct aagcatgtga aggactgtgc aactatggta    180
agacactatc taagagctga acacaagca ttaagcatgc ctgcatatat taaagctagg    240
tgcaagctgg caactgggga aggaagctgg aagtctatcc taactttttt taactatcag    300
aatattgaat taattacctt tattaatgct ttaaagctct ggctaaaagg aattccaaaa    360
aaaaactgtt tagcatttat tggccctcca aacacaggca agtctatgct ctgcaactca    420
ttaattcatt ttttgggtgg tagtgtttta tcttttgcca accataaaag tcacttttgg    480
cttgcttccc tagcagatac tagagctgct ttagtagatg atgctactca tgcttgctgg    540
aggtactttg acacataccct cagaaatgca ttggatggct accctgtcag tattgataga    600
aaacacaaag cagcggttca aattaaagct ccaccctcc tggtaaccag taatattgat    660
gtgcaggcag aggacagata tttgtacttg catagtcggg tgcaaacctt tcgctttgag    720
cagccatgca cagatgaatc gggtgagcaa ccttttaata ttactgatgc agattggaaa    780 tcttttttg taaggttatg ggggcgttta gacctg                               816

<210> SEQ ID NO 5
<211> LENGTH: 605
<212> TYPE: PRT
<213> ORGANISM: Artificial Sequence
<220> FEATURE:
<223> OTHER INFORMATION: The full-length protein amino acid sequence of
      wild-type bovine papillomavirus double-strand DNA helicase E1

<400> SEQUENCE: 5

Met Ala Asn Asp Lys Gly Ser Asn Trp Asp Ser Gly Leu Gly Cys Ser
1               5                   10                  15

-continued

```
Tyr Leu Leu Thr Glu Ala Glu Cys Glu Ser Asp Lys Glu Asn Glu Glu
             20                  25                  30

Pro Gly Ala Gly Val Glu Leu Ser Val Glu Ser Asp Arg Tyr Asp Ser
         35                  40                  45

Gln Asp Glu Asp Phe Val Asp Asn Ala Ser Val Phe Gln Gly Asn His
     50                  55                  60

Leu Glu Val Phe Gln Ala Leu Glu Lys Lys Ala Gly Glu Glu Gln Ile
 65                  70                  75                  80

Leu Asn Leu Lys Arg Lys Val Leu Gly Ser Ser Gln Asn Ser Ser Gly
                 85                  90                  95

Ser Glu Ala Ser Glu Thr Pro Val Lys Arg Lys Ser Gly Ala Lys
             100                 105                 110

Arg Arg Leu Phe Ala Glu Asn Glu Ala Asn Arg Val Leu Thr Pro Leu
         115                 120                 125

Gln Val Gln Gly Glu Gly Gly Arg Gln Glu Leu Asn Glu Glu Gln
     130                 135                 140

Ala Ile Ser His Leu His Leu Gln Leu Val Lys Ser Lys Asn Ala Thr
145                 150                 155                 160

Val Phe Lys Leu Gly Leu Phe Lys Ser Leu Phe Leu Cys Ser Phe His
                 165                 170                 175

Asp Ile Thr Arg Leu Phe Lys Asn Asp Lys Thr Thr Asn Gln Gln Trp
             180                 185                 190

Val Leu Ala Val Phe Gly Leu Ala Glu Val Phe Phe Glu Ala Ser Phe
         195                 200                 205

Glu Leu Leu Lys Lys Gln Cys Ser Phe Leu Gln Met Gln Lys Arg Ser
210                 215                 220

His Glu Gly Gly Thr Cys Ala Val Tyr Leu Ile Cys Phe Asn Thr Ala
225                 230                 235                 240

Lys Ser Arg Glu Thr Val Arg Asn Leu Met Ala Asn Met Leu Asn Val
             245                 250                 255

Arg Glu Glu Cys Leu Met Leu Gln Pro Pro Lys Ile Arg Gly Leu Ser
         260                 265                 270

Ala Ala Leu Phe Trp Phe Lys Ser Ser Leu Ser Pro Ala Thr Leu Lys
     275                 280                 285

His Gly Ala Leu Pro Glu Trp Ile Arg Ala Gln Thr Thr Leu Asn Glu
 290                 295                 300

Ser Leu Gln Thr Glu Lys Phe Asp Phe Gly Thr Met Val Gln Trp Ala
305                 310                 315                 320

Tyr Asp His Lys Tyr Ala Glu Glu Ser Lys Ile Ala Tyr Glu Tyr Ala
             325                 330                 335

Leu Ala Ala Gly Ser Asp Ser Asn Ala Arg Ala Phe Leu Ala Thr Asn
         340                 345                 350

Ser Gln Ala Lys His Val Lys Asp Cys Ala Thr Met Val Arg His Tyr
     355                 360                 365

Leu Arg Ala Glu Thr Gln Ala Leu Ser Met Pro Ala Tyr Ile Lys Ala
 370                 375                 380

Arg Cys Lys Leu Ala Thr Gly Glu Gly Ser Trp Lys Ser Ile Leu Thr
385                 390                 395                 400

Phe Phe Asn Tyr Gln Asn Ile Glu Leu Ile Thr Phe Ile Asn Ala Leu
             405                 410                 415

Lys Leu Trp Leu Lys Gly Ile Pro Lys Lys Asn Cys Leu Ala Phe Ile
         420                 425                 430

Gly Pro Pro Asn Thr Gly Lys Ser Met Leu Cys Asn Ser Leu Ile His
```

```
                435                 440                 445
Phe Leu Gly Gly Ser Val Leu Ser Phe Ala Asn His Lys Ser His Phe
    450                 455                 460
Trp Leu Ala Ser Leu Ala Asp Thr Arg Ala Ala Leu Ile Asp Asp Ala
465                 470                 475                 480
Thr His Ala Cys Trp Arg Tyr Phe Asp Thr Tyr Leu Arg Asn Ala Leu
                485                 490                 495
Asp Gly Tyr Pro Val Ser Ile Asp Arg Lys His Lys Ala Ala Val Gln
            500                 505                 510
Ile Lys Ala Pro Pro Leu Leu Val Thr Ser Asn Ile Asp Val Gln Ala
            515                 520                 525
Glu Asp Arg Tyr Leu Tyr Leu His Ser Arg Val Gln Thr Phe Arg Phe
            530                 535                 540
Glu Gln Pro Cys Thr Asp Glu Ser Gly Glu Gln Pro Phe Asn Ile Thr
545                 550                 555                 560
Asp Ala Asp Trp Lys Ser Phe Phe Val Arg Leu Trp Gly Arg Leu Asp
                565                 570                 575
Leu Ile Asp Glu Glu Glu Asp Ser Glu Glu Asp Gly Asp Ser Met Arg
            580                 585                 590
Thr Phe Thr Cys Ser Ala Arg Asn Thr Asn Ala Val Asp
            595                 600                 605

<210> SEQ ID NO 6
<211> LENGTH: 300
<212> TYPE: PRT
<213> ORGANISM: Artificial Sequence
<220> FEATURE:
<223> OTHER INFORMATION: The amino acid sequence of mutant 1 (K421L)
      E1-2 (306-605)

<400> SEQUENCE: 6

Leu Gln Thr Glu Lys Phe Asp Phe Gly Thr Met Val Gln Trp Ala Tyr
1               5                   10                  15
Asp His Lys Tyr Ala Glu Glu Ser Lys Ile Ala Tyr Glu Tyr Ala Leu
            20                  25                  30
Ala Ala Gly Ser Asp Ser Asn Ala Arg Ala Phe Leu Ala Thr Asn Ser
        35                  40                  45
Gln Ala Lys His Val Lys Asp Cys Ala Thr Met Val Arg His Tyr Leu
    50                  55                  60
Arg Ala Glu Thr Gln Ala Leu Ser Met Pro Ala Tyr Ile Lys Ala Arg
65                  70                  75                  80
Cys Lys Leu Ala Thr Gly Glu Gly Ser Trp Lys Ser Ile Leu Thr Phe
                85                  90                  95
Phe Asn Tyr Gln Asn Ile Glu Leu Ile Thr Phe Ile Asn Ala Leu Lys
            100                 105                 110
Leu Trp Leu Leu Gly Ile Pro Lys Lys Asn Cys Leu Ala Phe Ile Gly
            115                 120                 125
Pro Pro Asn Thr Gly Lys Ser Met Leu Cys Asn Ser Leu Ile His Phe
        130                 135                 140
Leu Gly Gly Ser Val Leu Ser Phe Ala Asn His Lys Ser His Phe Trp
145                 150                 155                 160
Leu Ala Ser Leu Ala Asp Thr Arg Ala Ala Leu Val Asp Asp Ala Thr
                165                 170                 175
His Ala Cys Trp Arg Tyr Phe Asp Thr Tyr Leu Arg Asn Ala Leu Asp
            180                 185                 190
```

```
Gly Tyr Pro Val Ser Ile Asp Arg Lys His Lys Ala Ala Val Gln Ile
            195                 200                 205

Lys Ala Pro Pro Leu Leu Val Thr Ser Asn Ile Asp Val Gln Ala Glu
        210                 215                 220

Asp Arg Tyr Leu Tyr Leu His Ser Arg Val Gln Thr Phe Arg Phe Glu
225                 230                 235                 240

Gln Pro Cys Thr Asp Glu Ser Gly Glu Gln Pro Phe Asn Ile Thr Asp
                245                 250                 255

Ala Asp Trp Lys Ser Phe Phe Val Arg Leu Trp Gly Arg Leu Asp Leu
            260                 265                 270

Ile Asp Glu Glu Glu Asp Ser Glu Glu Asp Gly Asp Ser Met Arg Thr
        275                 280                 285

Phe Thr Cys Ser Ala Arg Asn Thr Asn Ala Val Asp
290                 295                 300

<210> SEQ ID NO 7
<211> LENGTH: 300
<212> TYPE: PRT
<213> ORGANISM: Artificial Sequence
<220> FEATURE:
<223> OTHER INFORMATION: The amino acid sequence of mutant 2 (H323W)
      E1-2

<400> SEQUENCE: 7

Leu Gln Thr Glu Lys Phe Asp Phe Gly Thr Met Val Gln Trp Ala Tyr
1               5                   10                  15

Asp Trp Lys Tyr Ala Glu Glu Ser Lys Ile Ala Tyr Glu Tyr Ala Leu
            20                  25                  30

Ala Ala Gly Ser Asp Ser Asn Ala Arg Ala Phe Leu Ala Thr Asn Ser
        35                  40                  45

Gln Ala Lys His Val Lys Asp Cys Ala Thr Met Val Arg His Tyr Leu
    50                  55                  60

Arg Ala Glu Thr Gln Ala Leu Ser Met Pro Ala Tyr Ile Lys Ala Arg
65                  70                  75                  80

Cys Lys Leu Ala Thr Gly Glu Gly Ser Trp Lys Ser Ile Leu Thr Phe
                85                  90                  95

Phe Asn Tyr Gln Asn Ile Glu Leu Ile Thr Phe Ile Asn Ala Leu Lys
            100                 105                 110

Leu Trp Leu Leu Gly Ile Pro Lys Lys Asn Cys Leu Ala Phe Ile Gly
        115                 120                 125

Pro Pro Asn Thr Gly Lys Ser Met Leu Cys Asn Ser Leu Ile His Phe
130                 135                 140

Leu Gly Gly Ser Val Leu Ser Phe Ala Asn His Lys Ser His Phe Trp
145                 150                 155                 160

Leu Ala Ser Leu Ala Asp Thr Arg Ala Ala Leu Val Asp Asp Ala Thr
            165                 170                 175

His Ala Cys Trp Arg Tyr Phe Asp Thr Tyr Leu Arg Asn Ala Leu Asp
        180                 185                 190

Gly Tyr Pro Val Ser Ile Asp Arg Lys His Lys Ala Ala Val Gln Ile
    195                 200                 205

Lys Ala Pro Pro Leu Leu Val Thr Ser Asn Ile Asp Val Gln Ala Glu
    210                 215                 220

Asp Arg Tyr Leu Tyr Leu His Ser Arg Val Gln Thr Phe Arg Phe Glu
225                 230                 235                 240

Gln Pro Cys Thr Asp Glu Ser Gly Glu Gln Pro Phe Asn Ile Thr Asp
                245                 250                 255
```

```
Ala Asp Trp Lys Ser Phe Phe Val Arg Leu Trp Gly Arg Leu Asp Leu
            260                 265                 270

Ile Asp Glu Glu Asp Ser Glu Glu Asp Gly Asp Ser Met Arg Thr
        275                 280                 285

Phe Thr Cys Ser Ala Arg Asn Thr Asn Ala Val Asp
        290                 295             300

<210> SEQ ID NO 8
<211> LENGTH: 915
<212> TYPE: DNA
<213> ORGANISM: Artificial Sequence
<220> FEATURE:
<223> OTHER INFORMATION: The DNA sequence of mutant 1 E1-2

<400> SEQUENCE: 8
ggatccttgc agaccgagaa attcgacttc ggaactatgg tgcaatgggc ctatgatcac      60
aaatatgctg aggagtctaa aatagcctat gaatatgctt tggctgcagg atctgatagc    120
aatgcacggg cttttttagc aactaacagc caagctaagc atgtgaagga ctgtgcaact    180
atggtaagac actatctaag agctgaaaca caagcattaa gcatgcctgc atatattaaa    240
gctaggtgca agctggcaac tggggaagga agctggaagt ctatcctaac tttttttaac    300
tatcagaata ttgaattaat tacctttatt aatgctttaa agctctggct actgggaatt    360
ccaaaaaaaa actgtttagc atttattggc cctccaaaca caggcaagtc tatgctctgc    420
aactcattaa ttcattttt gggtggtagt gttttatctt ttgccaacca taaaagtcac    480
ttttggcttg cttccctagc agatactaga gctgctttag tagatgatgc tactcatgct    540
tgctggaggt actttgacac atacctcaga aatgcattgg atggctaccc tgtcagtatt    600
gatagaaaac acaaagcagc ggttcaaatt aaagctccac ccctcctggt aaccagtaat    660
attgatgtgc aggcagagga cagatatttg tacttgcata gtcgggtgca aaccttttcgc   720 tttgagcagc catgcacaga tgaatcgggt gagcaacctt ttaatattac tgatgcagat    780
tggaaatctt ttttttgtaag gttatggggg cgtttagacc tgattgacga ggaggaggat    840
agtgaagagg atggagacag catgcgaacg tttacatgta gcgcaagaaa cacaaatgca    900
gttgattaac tcgag                                                     915

<210> SEQ ID NO 9
<211> LENGTH: 912
<212> TYPE: DNA
<213> ORGANISM: Artificial Sequence
<220> FEATURE:
<223> OTHER INFORMATION: The DNA sequence of mutant 2 E1-2

<400> SEQUENCE: 9
ggatccttgc agaccgagaa attcgacttc ggaactatgg tgcaatgggc ctatgattgg     60
aaatatgctg aggagtctaa aatagcctat gaatatgctt tggctgcagg atctgatagc    120
aatgcacggg cttttttagc aactaacagc caagctaagc atgtgaagga ctgtgcaact    180
atggtaagac actatctaag agctgaaaca caagcattaa gcatgcctgc atatattaaa    240
gctaggtgca agctggcaac tggggaagga agctggaagt ctatcctaac tttttttaac    300
tatcagaata ttgaattaat tacctttatt aatgctttaa agctctggct aggaattcca    360
aaaaaaaact gtttagcatt tattggcccct ccaaacacag gcaagtctat gctctgcaac    420
tcattaattc attttttggg tggtagtgtt ttatcttttg ccaaccataa aagtcacttt    480
tggcttgctt ccctagcaga tactagagct gctttagtag atgatgctac tcatgcttgc    540
```

```
tggaggtact tgacacata cctcagaaat gcattggatg gctaccctgt cagtattgat    600
agaaaacaca aagcagcggt tcaaattaaa gctccacccc tcctggtaac cagtaatatt    660
gatgtgcagg cagaggacag atatttgtac ttgcatagtc gggtgcaaac ctttcgcttt    720
gagcagccat gcacgatga atcgggtgag caaccttta atattactga tgcagattgg     780 aaatctttt ttgtaaggtt atggggcgt ttagacctga ttgacgagga ggaggatagt     840
gaagaggatg gagacagcat gcgaacgttt acatgtagcg caagaaacac aaatgcagtt   900
gattaactcg ag                                                        912
```

<210> SEQ ID NO 10
<211> LENGTH: 24
<212> TYPE: DNA
<213> ORGANISM: Artificial Sequence
<220> FEATURE:
<223> OTHER INFORMATION: Forward Primer

<400> SEQUENCE: 10

```
cgggatcctt gcagaccgag aaat                                           24
```

<210> SEQ ID NO 11
<211> LENGTH: 46
<212> TYPE: DNA
<213> ORGANISM: Artificial Sequence
<220> FEATURE:
<223> OTHER INFORMATION: Reverse Primer

<400> SEQUENCE: 11

```
ccgctcgagt taatgatgat ggtgatgatg caggtctaaa cgcccc                   46
```

<210> SEQ ID NO 12
<211> LENGTH: 53
<212> TYPE: DNA
<213> ORGANISM: Artificial Sequence
<220> FEATURE:
<223> OTHER INFORMATION: Forward Primer 2

<400> SEQUENCE: 12

```
agttctgttc caggggcccc tgggatcctt gcagaccgag aaattcgact tcg           53
```

<210> SEQ ID NO 13
<211> LENGTH: 75
<212> TYPE: DNA
<213> ORGANISM: Artificial Sequence
<220> FEATURE:
<223> OTHER INFORMATION: Reverse Primer 2

<400> SEQUENCE: 13

```
tcagtcagtc acgatgcggc cgctcgagtt aatcaactgc atttgtgttt cttgcgctac    60
atgtaaacgt tcgca                                                     75
```

<210> SEQ ID NO 14
<211> LENGTH: 53
<212> TYPE: DNA
<213> ORGANISM: Artificial Sequence
<220> FEATURE:
<223> OTHER INFORMATION: Forward Primer 3

<400> SEQUENCE: 14

```
agttctgttc caggggcccc tgggatcctt gcagaccgag aaattcgact tcg           53
```

<210> SEQ ID NO 15

```
<211> LENGTH: 75
<212> TYPE: DNA
<213> ORGANISM: Artificial Sequence
<220> FEATURE:
<223> OTHER INFORMATION: Reverse Primer 3

<400> SEQUENCE: 15
tcagtcagtc acgatgcggc cgctcgagtt aatcaactgc atttgtgttt cttgcgctac    60
atgtaaacgt tcgca                                                    75

<210> SEQ ID NO 16
<211> LENGTH: 48
<212> TYPE: DNA
<213> ORGANISM: Artificial Sequence
<220> FEATURE:
<223> OTHER INFORMATION: 48nt-DNA sequence

<400> SEQUENCE: 16
ttttttttta aaaattttt tgggggtttt tttcccccct tttttttt                  48

<210> SEQ ID NO 17
<211> LENGTH: 44
<212> TYPE: DNA
<213> ORGANISM: Artificial Sequence
<220> FEATURE:
<223> OTHER INFORMATION: 44nt-DNA sequence

<400> SEQUENCE: 17
agctccaccc ctcctggtaa ccagtttttt tttttttttt tttt                    44

<210> SEQ ID NO 18
<211> LENGTH: 44
<212> TYPE: DNA
<213> ORGANISM: Artificial Sequence
<220> FEATURE:
<223> OTHER INFORMATION: 44nt-DNA sequence 1

<400> SEQUENCE: 18
tttttttttt tttttttttt ctggttacca ggaggggtgg agct                    44

<210> SEQ ID NO 19
<211> LENGTH: 24
<212> TYPE: DNA
<213> ORGANISM: Artificial Sequence
<220> FEATURE:
<223> OTHER INFORMATION: 24nt-DNA sequence

<400> SEQUENCE: 19
ctggttacca ggaggggtgg agct                                          24

<210> SEQ ID NO 20
<211> LENGTH: 22
<212> TYPE: DNA
<213> ORGANISM: Artificial Sequence
<220> FEATURE:
<223> OTHER INFORMATION: Labeled DNA sequence

<400> SEQUENCE: 20
cctacgccac cagctccgta gg                                            22

<210> SEQ ID NO 21
<211> LENGTH: 42
<212> TYPE: DNA
<213> ORGANISM: Artificial Sequence
<220> FEATURE:
<223> OTHER INFORMATION: non-labeled DNA sequence
```

<400> SEQUENCE: 21
cctacggagc tggtggcgta ggtttttttt tttttttttt tt                42

<210> SEQ ID NO 22
<211> LENGTH: 22
<212> TYPE: DNA
<213> ORGANISM: Artificial Sequence
<220> FEATURE:
<223> OTHER INFORMATION: The sequence of dsDNA with dspacer

<400> SEQUENCE: 22
tttttttttt tttttttttt tt                                     22

<210> SEQ ID NO 23
<211> LENGTH: 20
<212> TYPE: DNA
<213> ORGANISM: Artificial Sequence
<220> FEATURE:
<223> OTHER INFORMATION: The sequence of dsDNA 1 with dspacer

<400> SEQUENCE: 23
aaaaaaaaaa aaaaaaaaaa                                        20

<210> SEQ ID NO 24
<211> LENGTH: 100
<212> TYPE: DNA
<213> ORGANISM: Artificial Sequence
<220> FEATURE:
<223> OTHER INFORMATION: The DNA sequence used in quantification trial
      by Q-PCR

<400> SEQUENCE: 24
caggcagagg acagatattt gtacttgcat agtcgggtgc aaacctttcg ctttgagcag    60
ccatgcacag atgaatcggg ttttttttttt tttttttttt                        100

<210> SEQ ID NO 25
<211> LENGTH: 80
<212> TYPE: DNA
<213> ORGANISM: Artificial Sequence
<220> FEATURE:
<223> OTHER INFORMATION: The DNA 1 sequence used in quantification trial
      by Q-PCR

<400> SEQUENCE: 25
cccgattcat ctgtgcatgg ctgctcaaag cgaaaggttt gcacccgact atgcaagtac    60
aaatatctgt cctctgcctg                                                80

<210> SEQ ID NO 26
<211> LENGTH: 20
<212> TYPE: DNA
<213> ORGANISM: Artificial Sequence
<220> FEATURE:
<223> OTHER INFORMATION: The Primer sequence used in quantification
      trial by Q-PCR

<400> SEQUENCE: 26
caggcagagg acagatattt                                        20

<210> SEQ ID NO 27
<211> LENGTH: 20
<212> TYPE: DNA
<213> ORGANISM: Artificial Sequence
<220> FEATURE:
<223> OTHER INFORMATION: The Primer sequence used in quantification -continued

```
         trial by Q-PCR

<400> SEQUENCE: 27
cccgattcat ctgtgcatgg                                              20
```

TRANSMEMBRANE NANOPORE WITH NUCLEIC ACID UNWINDING FUNCTION AND ITS CONSTRUCTION METHODS AND APPLICATIONS

CROSS-REFERENCE TO RELATED APPLICATIONS

This application is a U.S. National Phase Application of PCT/CN2018/073716, filed Jan. 23, 2018, which claims priority to CN 201710060033.9, filed Jan. 24, 2017, the contents of which applications are incorporated herein by reference in their entireties for all purposes.

SEQUENCE LISTING STATEMENT

Incorporated herein by reference in its entirety is a Sequence Listing named "C127820052 SequenceListing", which is being submitted to the USPTO via EFS-web on even date herewith as an ASCII text file 24.8 KB in size. This file, which was created on Jul. 21, 2019, constitutes both the paper and computer readable form of the Sequence Listing.

FIELD OF THE INVENTION

This invention belongs to the field of biotechnology, in particular to a transmembrane nanopore with nucleic acid unwinding function and its construction method and application.

BACKGROUND OF THE INVENTION

Accurately detection of biological and chemical active substances is one of the targets of industry and scientific research through ages, which requires robust and stable sensors. Since the first application of α-hemolysin (α-HL) in the field of single molecule detection, nanopores, as a technical platform for single molecule detection, have been playing an increasingly important role.

Binding or "capturing" the interested analytes for detection via intermolecular affinity interactions (e.g. covalent binding or noncovalent attraction), for example, specifically distinguish and quantify the divalent metal ions such as nickel, copper, and zinc by inserting histidine into the (3-barrel district of α-HL; small organic molecules and even fractions of proteins can be detected by embedding specific ligands into inner nanopores through gene engineering, amino acid configurations can also be differentiated via combining copper ion with cysteine (117) of α-HL nanopore.

Besides α-HL, other researched protein nanopores contains alamethicin-used for detection of polyethylene glycol, *Mycobacterium smegmatis* recombinant protein MspA- widely used for high throughput nucleic acid sequencing at present, bacteriophage phi29 DNA packaged motor protein-allowing double strands to pass by, etc. The nanopore of these proteins, such as α-HL and MspA, requires other enzymes for assists to complete the detection of analytes, which limits its further application.

From the existing research reports, when the α-HL nanopore, which with the narrowest diameter of 1.5 nm in the transmembrane (3-barrel district and the length of 5.2 nm, was used for sequencing or sensing of other small molecules, the length at the narrowest part of nanopore was too long to make the nucleic acid chain ratchet through the nanopore, as a result, it was difficult to distinguish single base, and the sensing resolution of other small molecules was therefore reduced.

Though the length of the transmembrane section of MspA is shorter than α-HL, it is usually only functioned as a nanopore, being equal to an artificial carbon nanotubes in sensing molecular, and existing as an ion channel. For example, Ian M, Elizabeth, etc. coupled Hel308 helicase or Φ129DNA polymerase with MspA to distinguish single base in nucleic acid.

The electrical signal from phi29 DNA packaged motor protein is easily interfered, when it detects trace substances, attributing to its poor voltage-gated characteristics.

Those skilled in the art are using other materials, such as synthetic metal or silicon nanopore, for potential application of sequencing, however, these synthetic nanopores are not reliable enough to produce consistent repetitive structures and lack diversity in chemical modification. Therefore, searching for better nanopores or their substitutions is still a hotspot and difficulty in this field.

SUMMARY OF THE INVENTION

The technical problem to be solved in the invention is to overcome the deficiency of the existing protein nanopore with small channel size which needs to externally unwind active components when transferring double-stranded nucleic acid.

This invention provides a monomeric protein to solve the deficiency mentioned above. The monomeric protein, (1) being consisted of amino acids from 306 to 577 position of isolated bovine papillomavirus double-strand DNA helicase, and its sequence is shown in SEQ ID No. 3, Or (2) being a variant obtained by substitution and/or deletion and/or insertion of at least one amino acid in the amino acid sequence of the protein defined in (1).

Furthermore, the monomeric protein in this invention is a variant obtained by substituting and/or deleting and/or inserting 1 to 20 amino acids in the amino acid sequence of the protein defined in (1).

Optimally, it is a variant obtained by substituting and/or deleting and/or inserting 1 to 15 amino acids in the amino acid sequence of the protein defined in (1).

Further, the above-mentioned protein is a variant obtained by substituting and/or deleting and/or inserting no more than 10 amino acids in the amino acid sequence of the protein defined in (1), owning the same or similar function with the monomeric protein.

Preferably, a restricted variant with (1) obtained by substituting and/or missing and/or inserting 1 to 10 amino groups in the amino acid sequence of the protein shown in (1).

Preferably, a restricted variant with (1) obtained by substituting and/or missing and/or inserting 1 to 5 amino groups in the amino acid sequence of the protein shown in (1).

Preferably, a restricted variant with (1) obtained by substituting and/or missing and/or inserting 1 to 3 amino groups in the amino acid sequence of the protein shown in (1).

Further, the above protein variant is the protein variant obtained from K mutation to L at 421, or from H mutation to W at 323 of the protein with amino acid sequence SEQ ID No. 3.

Preferred: The above protein variant is a homologous variant, which has more than amino acid sequence homology of 75% with the sequence of SEQ ID No. 3 as defined in (1).

Preferred: The above protein variant is a homologous variant, which has more than amino acid sequence homology of 80% with the sequence of SEQ ID No. 3 as defined in (1).

More preferred: The above protein variant is a homologous variant, which has more than amino acid sequence homology of 90% with the sequence of SEQ ID No. 3 as defined in (1).

Re-optimization: The above protein variant is a homologous variant, which has more than amino acid sequence homology of 95% with the sequence of SEQ ID No. 3 as defined in (1).

Further optimization: The above protein variant is a homologous variant, which has more than amino acid sequence homology of 98% with the sequence of SEQ ID No. 3 as defined in (1).

Optimal: The above protein variant is a homologous variant, which has more than amino acid sequence homology of 99% with the sequence of SEQ ID No. 3 as defined in (1).

The present invention also provides genes encoding the above-mentioned proteins.

Further, the nucleotide sequence of the above genes is shown in SEQ ID No. 4.

At the same time, the invention also provides vectors containing the above genes.

Of course, the present invention also provides host cells containing the above vectors.

The invention also provides another protein, (1) being consisted of amino acids from 306 to 605 position of isolated bovine papillomavirus double-strand DNA helicase, its sequence is shown in SEQ ID No. 1; or (2): being a variant obtained by substitution and/or deletion and/or insertion of at least one amino acid in the amino acid sequence of the protein defined in (1).

Further, the monomer protein is a variant obtained by substituting and/or deleting and/or inserting of 1 to 20 amino acids in the amino acid sequence of the defined in (1).

Preferably, the monomer protein is a variant obtained by substituting and/or deleting and/or inserting 1 to 15 amino acids in the amino acid sequence of the protein defined in (1).

Further, the above proteins are protein with the same or similar function as that of the monomer protein obtained by substituting and/or deleting and/or inserting no more than 10 amino acids in the amino acid sequence of the protein defined in (1).

Preferably, the monomer protein is a variant obtained by substituting and/or deleting and/or inserting 1 to 10 amino acids in the amino acid sequence of the protein defined in (1).

Re-optimally, the monomer protein is a variant obtained by substituting and/or deleting and/or inserting 1 to 5 amino acids in the amino acid sequence of the protein defined in (1).

More optimally, the monomer protein is a variant obtained by substituting and/or deleting and/or inserting 1 to 3 amino acids in the amino acid sequence of the protein defined in (1).

Preferred: the above protein variant is a homologous variant, which has more than amino acid sequence homology of 75% with sequence of SEQ ID No. 1 as defined in (1).

Preferred: the above protein variant is a homologous variant, which has more than amino acid sequence homology of 80% with sequence of SEQ ID No. 1 as defined in (1).

More optimally, the above protein variant is a homologous variant, which has more than amino acid sequence homology of 90% with sequence of SEQ ID No. 1 as defined in (1).

Re-optimally, the above protein variant is a homologous variant, which has more than amino acid sequence homology of 95% with sequence of SEQ ID No. 1 as defined in (1).

Further preferably, the above protein variant is a homologous variant, which has more than amino acid sequence homology of 98% with sequence of SEQ ID No. 1 as defined in (1).

Most preferably, the above protein variant is a homologous variant, which has more than amino acid sequence homology of 99% with sequence of SEQ ID No. 1 as defined in (1).

Further, the above protein is the protein variant obtained from K mutation to L at 421, or from H mutation to W at 323 of the protein with amino acid sequence shown in SEQ ID No. 1.

Further, the amino acid sequences of the protein variants are shown in SEQ ID No. 6 and SEQ ID No. 7 respectively.

The present invention also provides genes encoding the above-mentioned protein.

Further, the nucleotide sequences of the above genes are shown in SEQ ID No. 2.

The invention also provides a coding gene of the protein variant. The nucleotide sequence is shown in SEQ ID No. 8 and SEQ ID No. 9 respectively.

At the same time, the invention also provides a vector containing the above genes.

Of course, the present invention also provides host cells containing the above vector.

In addition, the invention also provides a polymer protein. The polymer protein contains more than two of the above-mentioned protein as subunits.

Furthermore, the number of subunits constituting the multimeric protein is 4-8.

Preferably, the number of subunits constituting the multimeric protein is 6.

Wherein, the above-mentioned polymer proteins are homomultimer or heteropolymer.

The invention also provides a use of the above-mentioned protein or polymer protein in the preparation of nanopore or membrane containing conductive pores.

The invention also provides a membrane containing conductive pores, it comprises: (1) a membrane layer; and (2) a separated above-mentioned polymer protein, which is embedded in the membrane layer to form a pore which can be electrically conducted through the pore when a transmembrane potential is applied.

Wherein, the membrane layer in the nanopore comprises a lipid layer.

Wherein, the lipid layer in the nanopore contains amphiphilic lipids.

Wherein, the lipid layer in the nanopore can be a planar membrane layer or a liposome.

Further, when the nanopore is applied potential, the conductive pore membrane can translocate DNA or RNA through the pore.

Preferably, the monolayer described in the above-mentioned membrane layer is formed by PMOXA-PDMS-PMOXA, PMOXA is dimethyl-diazolin, and PDMS is polydimethylsiloxane.

In addition, the invention also provides a method for preparing a membrane containing conductive pores, which is characterized by the following steps:
(a) Preparing dried amphiphilic lipids;
And (b) resuspending the dried amphiphilic lipids in a solution comprising aqueous solvent, penetrating agent and several separated proteins mentioned above, the protein as subunits can be self-assembled into hexamer protein, which can insert into lipid bilayer membrane under certain conditions and sufficient time to form a membrane containing conductive pore. Preferably, the polymer protein is a hexamer.

Wherein, the amphiphilic lipids mentioned above are phospholipids.

Wherein, the phospholipids mentioned above is selected from one or more of the phospholipids listed below: phosphatidylcholine, phosphatidylethanolamine, phosphatidylserine serine, phosphatidylinositol, phosphatidylglycerol, cardiolipid, 1,2-diphytyl-sn-glycerol-3-phosphatidylcholine, and 1,2-diphenyl-sn-glycerol-3-phosphatidylcholine.

The invention also provides a use of nanopore in the preparation of single-molecule sensor or kits.

The invention also provides a single molecule sensor or a reagent kit, which contains the nanopore as one of the components.

The invention also provides an application of bovine papillomavirus double-stranded DNA helicase protein or its homologous protein in preparation of nanopore or membrane containing conductive pore. The amino acid sequence of the bovine papillomavirus double-stranded DNA helicase protein is shown in SEQ ID No. 5. Further, the homologous proteins of the bovine papillomavirus double-stranded DNA helicase protein are selected from table 1 below.

TABLE 1

| Homologous protein | |
| --- | --- |
| Sources of homologous protein | NCBI accession number |
| Bovine papillomavirus -1 | NP_056739.1 |
| Bovine papillomavirus -1 | AAB35071.1 |
| Bovine papillomavirus -1 | AFV52373.1 |
| Delta papillomavirus genus -4 | ACR78098.1 |
| Delta papillomavirus genus -4 | ACR78091.1 |
| Delta papillomavirus genus -4 | ACR78081.1 |
| Dairy cow papillomavirus -13 | YP_009272574.1 |
| Bovine papillomavirus -13 | AIN81126.1 |
| Bovine papillomavirus -2 | AGR88554.1 |
| Bovine papillomavirus -2 | AMZ04139.1 |
| Bos grunniens papillomavirus -1 | AFQ90258.1 |
| Bovine papillomavirus -14 | AKB94040.1 |

The invention also provides a membrane containing conductive pores, includes: (1) a membrane layer;
And (2) a separated bovine papillomavirus double-stranded DNA helicase protein or its homologous protein, the multimeric protein is embedded in the membrane layer to form pore, which can be electrically conducted when a bias voltage is applied, the amino acid sequence of the double-stranded DNA helicase protein of bovine papillomavirus is shown in SEQ ID No. 5

The homologous protein of the bovine papillomavirus double-stranded DNA helicase protein is selected from table 1.

The key component protein in the mammalian pathogenic virus was modified firstly by protein engineering technology in this invention, so that it can be used to construct a novel protein nanopore for the sensing research of nucleic acid and other substances. The invention expresses and purifies the protein in vitro by prokaryotic expression system, and simultaneously embeds it on the artificial phospholipid bilayer membrane and the polymer membrane to become a protein nanopore. By studying its conductance distribution under various conductivity buffer systems, as well as the transport of single-stranded DNA and single-stranded RNA, and its helicase activity, a novel nanopore sensing system combining the characteristics of porin and the helicase activity of proteins was constructed firstly, and the untwisting and translocation of double-stranded DNA with a single arm was realized on the lipid bilayer.

The beneficial effects of the invention are as follows:

The present invention finds that the bovine papillomavirus double-stranded DNA helicase protein and its homologous protein can be used to prepare a membrane containing conductive pore, it provides a new effective choice for this field.

The present invention discovers the E1-1 (306-577) protein innovatively, which forms a polymer acting as a new and simple membranes containing conductive pore, and we verified it can be stable presence on phospholipid double-layered membranes and it has the characteristics of translocation nucleic acids.

The invention further discovers the new protein E1-2 (306-605), and successfully constructs a nanopore and helicase integrated sensing system based on it, which replaces the existing sensing method that needs to couple the helicase and the nanopore, and it can be used as a biosensor. Compared with the current phi29 and MspA, Hel308 and MspA, and the coupled sensing systems of phi29 and α-HL, the nanopore of the present invention can realize the single enzyme to complete the capture of analytes to be measured, through the pore, which greatly simplify the steps. In particular, the nanopore can simultaneously perform unwinding of double-stranded DNA and analysis of sensing, analysis of nucleic acid polymorphism, analysis of nucleic acid secondary structure, analysis of nucleic acid length, etc. In terms of medicinal use, its potential-driven solute translocation can also be applied to liposome drug delivery therapy (e.g. drug targeted delivery), which has great potential for application.

The invention further carries out mutation research on the molecular basis of the E1-2 protein, and obtains a mutant of the E1-2 protein. The pores formed by the mutant E1-1 (306-577) monomer or E1-2 (306-605) monomer on the artificial lipid membrane have many advantages over the wild type. Specifically, the pores constructed from the mutant monomers are more likely to capture nucleic acids and other small molecules with negatively charged than the wild type. In addition, the pores constructed from the mutant monomers exhibit an increase in current range, which makes the lumen of the pores narrower than that of the wild type, thereby making the pore detection current more extensive and sensitive.

DETAILED DESCRIPTION OF THE PREFERRED EMBODIMENTS

Figure 1:
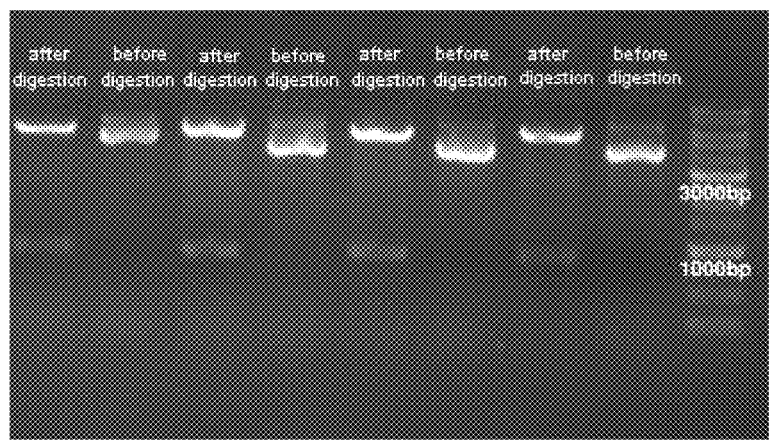
FIG. 1: The recombinant plasmid E1-1 (306-577) of the target gene was constructed using pGEX-6P-1 as the vector for verification by agarose gel electrophoresis (pGEX-6p-1 was 4984 bp in length, and the E1-1 gene sequence was 816 bp in length, so two bands were obtained after digestion. They were 4990 bp and 822 bp, respectively).

The invention is described in conjunction with the drawings below.

The object of the invention is initiated by a hexamer cyclic helicase of bovine papillomavirus, which plays a role of assisting genomic DNA replication in bovine papillomavirus. Wild-type protein is an ATP-dependent helicase of bovine papillomavirus that exists for melting DNA of a double-helix during viral replication. It is reported that the protein binds to single-stranded DNA and attaches to the genomic DNA replication initiation site in a hexamer form at the initiation of viral genome replication. And under the condition of energy provided by atpase hydrolysis of ATP, it continues to melt along the single-stranded DNA from the replication fork in the 3'-5' direction.

The full-length protein amino acid sequence (SEQ ID No. 5) of wild-type bovine papillomavirus double-strand DNA helicase E1, has 605 amino acids in total. The italicized and underlined part is E1-1 (306-577):

Mandkgsnwdsglgcsyllteaecesdkeneepgagvelsvesdrydsqd
edfvdnasvfqgnhlevfqalekkageeqilnlkrkylgssqnssgseas
etpvkrrksgakrrlfaeneanrvltplqvqgegegrqelneeqaishlh
lqlyksknatvfklglfkslflcsfhditrlfkndkttnqqwvlavfgl
aevffeasfellkkqcsflqmqkrsheggtcavylicfntaksretvrnl
manmlnvreeclmlqppkirglsaalfwfksslspatlkhgalpewiraq
ttlnes*lqtekfdfgtmvqwaydhkyaeeskiayeyalaagsdsnarafl*
*atnsqakhvkdcatmvrhylraetqalsmpayikarcklatgegswksil*
*tffnyqniehtitfinalklwlkgipkknclafigppntgksmlcnslih*
*flggsvlsfanhkshfwlasladtraaliddathacwryfdtylrnaldg*
*ypvsidrkhkaavqikappllvtsnidvqaedrylylhsrvqtfrfeqpc*
*tdesgeqpfnitdadwksffvrlwgrldl*ideeedseedgdsmrtftcsa
rntnavd.

The invention discovers that the bovine papillomavirus double-stranded DNA helicase protein and its homologous protein can be used to prepare nanopores and membranes containing conductive pore. The prepared nanopore and the membrane containing conductive pore can be used for the preparation of a single molecule sensor or kit for characterizing a target sample. It provides a new and effective choice for the field.

The optional information of the bovine papillomavirus double-stranded DNA helicase protein is shown in table 2 below:

TABLE 2

Information of bovine papillomavirus double-stranded DNA helicase protein

| Homologous protein name | Source | NCBI accession number | Similar mutated amino acid |
|---|---|---|---|
| E1 | Bovine papillomavirus -1 | NP_056739.1 | Compare the homologous protein with the bovine papillomavirus double-strand DNA helicase E1 described in the invention (NCBI accession number P03116), the sequence similarity is found to be 100%. Therefore, the protein could also adopt the following mutation scheme to improve the pore performance. |
| E1 replication protein | Bovine papillomavirus -1 | AAB35071.1 | Compare the homologous protein with the bovine papillomavirus double-stranded DNA helicase E1 described in the invention (NCBI accession number P03116), the sequence similarity is found to be 100%. Therefore, the protein could also adopt the following mutation scheme to improve the pore performance. |
| E1 | Bovine papillomavirus -1 | AFV52373.1 | Compare the homologous protein with the bovine papillomavirus double-strand DNA helicase E1 described in the invention (NCBI accession number P03116), the sequence similarity is found to be 100%. Therefore, the protein could also adopt the following mutation scheme to improve the pore performance. |
| E1 | Delta papillomavirus genus -4 | ACR78098.1 | Compare the homologous protein with the bovine papillomavirus double-strand DNA helicase E1 described in the invention (NCBI accession number P03116), the sequence similarity is >99%, and the above-mentioned mutant amino acid position is same as E1-2 (306-605). Therefore, the protein could also adopt the following mutation scheme to improve the pore performance. |
| E1 | Delta papillomavirus genus -4 | ACR78091.1 | Compare the homologous protein with the bovine papillomavirus double-stranded DNA helicase E1 described in the invention (NCBI accession number P03116), the sequence similarity is >98%, and the above-mentioned mutant amino acid position is same as E1-2 (306-605). Therefore, the protein could also adopt the following mutation scheme to improve the pore performance. |
| E1 | Delta papillomavirus genus -4 | ACR78081.1 | Compare the homologous protein with the bovine papillomavirus double-stranded DNA helicase E1 described in the invention (NCBI accession number P03116), the sequence |

TABLE 2-continued

Information of bovine papillomavirus double-stranded DNA helicase protein

| Homologous protein name | Source | NCBI accession number | Similar mutated amino acid |
|---|---|---|---|
| E1 protein | Bovine papillomavirus-13 | YP_009272574.1 | similarity is >98%, and the above-mentioned mutant amino acid position is same as E1-2 (306-605). Therefore, the protein could also adopt the following mutation scheme to improve the pore performance. Compare the homologous protein with the bovine papillomavirus double-stranded DNA helicase E1 described in the invention (NCBI accession number P03116), the sequence similarity is >98%. Compare the above-mentioned mutant amino acid with E1-2 (306-605), aspartic acid (D) was replaced by glutamate (E) at amino acid 530 as a homologous replacement. Therefore, the protein could also adopt the following mutation scheme to improve the pore performance. |
| E1 regulatory protein | Bovine papillomavirus-13 | AIN81126.1 | Compare the homologous protein with the bovine papillomavirus double-stranded DNA helicase E1 described in the invention (NCBI accession number P03116), the sequence similarity is >98%. Compare the above-mentioned mutant amino acid with E1-2 (306-605), aspartic acid (D) was replaced by glutamate (E) at amino acid 530 as a homologous replacement. Therefore, the protein could also adopt the following mutation scheme to improve the pore performance. |
| E1 protein | Bovine papillomavirus-2 | AGR88554.1 | Compare the homologous protein with the bovine papillomavirus double-stranded DNA helicase E1 described in the invention (NCBI accession number P03116), the sequence similarity is >97%, and the above-mentioned mutant amino acid position is same as E1-2 (306-605). Therefore, the protein could also adopt the following mutation scheme to improve the pore performance. |
| E1 | Bovine papillomavirus-2 | AMZ04139.1 | Compare the homologous protein with the bovine papillomavirus double-stranded DNA helicase E1 described in the invention (NCBI accession number P03116), the sequence similarity is >97%, and the above-mentioned mutant amino acid position is same as E1-2 (306-605). Therefore, the protein could also adopt the following mutation scheme to improve the pore performance. |
| E1 protein | Bovine papillomavirus-1 | AFQ90258.1 | Compare the homologous protein with the bovine papillomavirus double-stranded DNA helicase E1 described in the invention (NCBI accession number P03116), the sequence similarity is >96%. Compare the above-mentioned mutant amino acid position with E1-2 (306-605), aspartic acid (D) was replaced by glutamate (E) at amino acid 530 as a homologous replacement. Therefore, the protein could also adopt the following mutation scheme to improve the pore performance. |
| E1 | Bovine papillomavirus-14 | AKB94040.1 | Compare the homologous protein with the bovine papillomavirus double-stranded DNA helicase E1 described in the invention (NCBI accession number P03116), the sequence similarity is >75%. Compare the above-mentioned mutant amino acid position with E1-2 (306-605), aspartic acid (D) was replaced by glutamate (E) at amino acid 530 as a homologous replacement; lysine (K) was replaced by arginine (R) at amino acid 417 as a |

TABLE 2-continued

Information of bovine papillomavirus double-stranded DNA helicase protein

| Homologous protein name | Source | NCBI accession number | Similar mutated amino acid |
| --- | --- | --- | --- |
| | | | homologous replacement; histidine (H) was replaced by asparagine (N) at amino acid 323 as a non-homologous replacement, The replacement from hydrophobic amino acids to hydrophilic ones is useless; Glutamate (E) was replaced by glycine (G) at amino acid 392, replacing acidic amino acids with neutral amino acids, which is not beneficially replaced; lysine (K) was replaced by leucine (L) at amino acid 396, replacing basic amino acids with neutral amino acids, which is not beneficially replaced; lysine (K) was replaced by Glutamate (E) at amino acid 387, replacing basic amino acids with acidic amino acid, which is not beneficially replaced; Therefore, the protein could also adopt the following mutation scheme to improve the pore performance. |

From the crystal structure and functional domain of the protein, we know that the conservative region of the protein is distributed in amino acids 1-121 and amino acids 166-575. In the two conservative regions, amino acids 407-557 are SF3 helicase functional domains, 413-457 amino acids belong to the AAA+ family of ATP hydrolases, and 142-308 amino acids are DNA binding domains. The amino acids 84-86 and 105-108 are respectively nucleic acid positioning signal regions; we identified some of the homologous proteins of these proteins, which have similar structures and same function (unwinding double-stranded DNA under the action of ATP hydrolysis energy). It is expected that these homologous proteins will also form stable pores on the artificial lipid membrane after adopting the described mutation and have the same on-membrane nucleic acid unwinding function as E1-1 (306-577), becoming a tool for the sensing of nucleic acid and small molecules.

According to the crystal structure analysis, the main helical functional domain of bovine papillomavirus double-stranded DNA helicase protein exists in the 308-577 amino acid segment. The invention constructs and purifies E1's truncated polypeptide E1-1 (306-577) in vitro. Using short-chained double-stranded DNA (dsDNA), the activity of ATP-dependent helicase in its hexamer is verified under specific conditions in vitro.

The invention further utilizes the truncated polypeptide E1-1 (306-577) to prepare nanopores. As mentioned in this invention, the hexameric pore completes the translocation of ssDNA, and the probability of translocation of single-stranded DNA (ssDNA) is slightly different.

The invention obtains another truncated body E1-2 (306-605) of E1 in further research. The protein can successfully form a stable nanopores on artificial lipid membrane under various conductive buffer conditions in vitro.

The invention also studies the following nucleic acid sensing using patch-clamp technology. Structural analysis shows that the inner diameter of the nanopore formed by E1-2 protein is about 1.3 nm, and the length of membrane region and the diameter of opening of the protein are about 3.2 nm and 15 nm respectively.

The experiment shown that under the buffer conditions of 1M, 0.3 mM KCl, and PBS, E1 (306-605) can self-assemble into a hexamer on an artificial lipid membrane and firmly form a pore on the membrane. After applying the transmembrane voltage on both sides of the membrane, generates a current passing through the pore. In the subsequent ssDNA transport experiment, it is found that short-chained ssDNA can trigger a series of current blocking phenomena, but using dsDNA to repeat the same experiment does not cause similar phenomena. The transmembrane current is stable, and these phenomena are consistent with the diameter of E1. The diameter of dsDNA is about 2 nm, while the inner diameter limit of E1 is about 1.3 nm, so when the dsDNA with flat end is driven by the transmembrane voltage, it is captured by E1. In most cases, either a continuously blocking with a blockage of more than 50% of the pore or the immediate opening of the pore after blocking occurs; When dsDNA with a single arm is captured by E1 driven by transmembrane voltage in PBS buffer or buffer with equal salt concentration as PBS, a specific concentration of ATP and $Mg^{2+}$ are added. Combined with E1's own helicase activity and its characteristics as a biological nanopore, it is shown that the double chain unwinding on the artificial lipid membrane was completed in vitro using the pore formed by E1-2 (306-605).

The mutants of E1-1 (306-577) and E1-2 (306-605) also have the same or similar functions and are also within the scope of protection of the invention.

It was found in the study that the mutants of E1-1 (306-577) and E1-2 (306-605) exhibited improved properties for subsequent nanopore incorporation and capture of negatively charged nucleic acids and ssDNA translocation. Specifically, the mutants show surprisingly easier artificial liposome insertion characteristics, stable presence on lipid membranes, and non-specific current fluctuations are further reduced due to the improvement of signal-to-noise ratio of open current caused by the pore. The capture efficiency of ssDNA at the C end of the pore was further improved. In the process of nucleic acid translocation, the inherent force of the pore cavity on ssDNA is weakened, and the translocation current presents a more rapid and regular peak pattern. Another advantage of the mutant is that the mutation does not affect the characteristics of the pore itself as a DNA helicase.

Therefore, the invention provides a mutated E1-1 (306-577) monomer or a mutated E1-2 (306-605) monomer, which contains variants of the amino acid sequence shown in SEQ ID NO.1 or SEQ ID NO.3. Wherein the variant contains at least one of the following mutations (the number of bits of each of the following mutation sites is calculated from the first position of the total length of bovine papilloma virus double-stranded DNA helicase. The total length amino acid sequence of bovine papilloma virus double-stranded DNA helicase is shown in SEQ ID No. 5):

(a) The amino acid at 479 position is histidine (H), lysine (K), serine (S), asparagine (N), threonine (T);

(b) The amino acid at 489 position is histidine (H), lysine (K), asparagine (N), threonine (T) and serine (S);

(c) The amino acid at 530 position is histidine (H), lysine (K), serine (S), asparagine (N), threonine (T);

(d) The amino acid at 529 position is glutamine (Q) and lysine (K);

(e) The amino acid at 525 position is histidine (H), lysine (K), serine (S), leucine (L), threonine (T);

(f) The amino acid at 504 position is asparagine (N), lysine (K), arginine (R), serine (S), threonine (T), phenylalanine (f), tyrosine (Y), tryptophan (W);

(g) The amino acid at 328 position is glutamine (Q), lysine (K), arginine (R), phenylalanine (F), tyrosine (Y), tryptophan (W);

(h) The amino acid at 360 position is asparagine (N), lysine (K), arginine (R), phenylalanine (F), tyrosine (Y), tryptophan (W);

(i) The amino acid at 322 position is asparagine (N), leucine (L), isoleucine (I), valine (V), phenylalanine (F), tryptophan (W), glutamine (Q);

(j) The amino acid at 372 position is glutamine (Q), leucine (L), isoleucine (I), valine (V), proline (P), phenylalanine (F), tryptophan (W), asparagine (N);

(k) The amino acid at 342 position is asparagine (N), leucine (L), isoleucine (I), valine (V), phenylalanine (F), tryptophan (W), glutamine (Q);

(l) The amino acid at 334 position is asparagine (N), leucine (l), isoleucine (I), valine (V), phenylalanine (F), tryptophan (W), glutamine (Q);

(m) The amino acid at 392 position is asparagine (N), leucine (L), isoleucine (I), valine (V), phenylalanine (F), tryptophan (W), glutamine (Q);

(n) The amino acid at 408 position is asparagine (N), leucine (L), isoleucine (I), valine (V), phenylalanine (F), tryptophan (W), glutamine (Q);

(o) The amino acid at 396 position is leucine (L), isoleucine (I), valine (V), phenylalanine (F) and tryptophan (W). Alanine (A) and glycine (G);

(p) The amino acid at 570 position is valine (V), phenylalanine (F), tryptophan (W), alanine (A), glycine (G), leucine (L), isoleucine (I);

(q) The amino acid at 574 position is tryptophan (W), alanine (A), glycine (G), leucine (L), isoleucine (I), valine (V) and phenylalanine (F);

(r) The amino acid at 417 position is leucine (L), isoleucine (I), valine (V), phenylalanine (F), tryptophan (W), alanine (A) and glycine (G);

(s) The amino acid at 421 position is Valine (V), phenylalanine (F), tryptophan (W), alanine (A), glycine (G), leucine (L) and isoleucine (I);

(t) The amino acid at 383 position is valine (V), phenylalanine (F), tryptophan (W), alanine (A), glycine (G), leucine (L), isoleucine (I);

(u) The amino acid at 387 position is histidine (H), phenylalanine (F), tryptophan (W);

(v) The amino acid at 323 position is leucine (L), isoleucine (I), valine (v), phenylalanine (F), tryptophan (W), alanine (A), glycine (G).

(w) The amino acid at 324 position is leucine (L), isoleucine (I), proline (P) and valine (V);

(x) The amino acid at 565 position is threonine (T), serine (S) and tyrosine (Y);

(y) The amino acid at 426 position is leucine (L), isoleucine (I), valine (V), phenylalanine (F), tryptophan (W), alanine (A), glycine (G).

The invention provides a mutated E1-1 (306-577) monomer or a mutated E1-2 (306-605) monomer. The above-mentioned E1-1 (306-577) variants or E1-2 (306-605) variant monomers can be used to form the conductive membrane pore in this invention. Mutated E1-1 (306-577) monomer or E1-2 (306-605) monomer is a monomer whose sequence is different from that of wild E1-1 (306-577) monomer or E1-2 (306-605) monomer and retains the ability of forming pore. The methods used to confirm the capability of mutant monomers to form pores are consistent with methods mentioned in this invention.

The mutant E1-1 (306-577) monomer or E1-2 (306-605) monomer has multiple advantages over a wild type monomer in forming a pore on artificial lipid membrane. Specifically, the pore constructed by mutated monomer is more likely to capture nucleic acids and other negatively charged small molecules than wild type, in addition it shows an increase in current range, making the inner cavity of the pore narrower than that of wild type, so that the current detection in the pore is more extensive and sensitive.

In addition, when the mutated E1-1 (306-577) or E1-2 (306-605) monomers form a pore on an artificial lipid membrane, the transmembrane region of the pore is more likely to stably exist on the membrane and the signal-to-noise ratio of open current is higher than that of wild type. Surprisingly, when nucleic acid moves through some pores constructed by mutated E1-1 (306-577) or E1-2 (306-605) monomers, the current decreases even more. This makes it possible to use this pore to identify the relationship between nucleic acid sequence and the current descent platform when the nucleic acid moves through the pore, and further makes this mutant pore have the potential to apply to nucleic acid sequencing in the future. The improvements of nucleic acid reading properties of the mutants are realized through three main mechanisms, namely through changing:

1. Space (the increase or decrease of mutated amino acid residues);
2. Charge (for example, induces +ev charge to enhance the interaction between nucleic acids and amino acids);
3. Non-covalent bonding (for example, induces amino acids that can bind with certain nucleotides with hydrogen bonds);

Either or more of these three mechanisms may be the reason why the pore of the invention has nucleotide reading property in the future.

The site mutation of the protein in the invention is mainly based on the following reasons:

In wild type E1-1 (306-577) or E1-2 (306-605), the N terminal is open at the narrower end, the C terminal is open at the wider end, and the hexamer forms a standard mushroom structure. A large number of alkaline amino acids are distributed in the inner cavity of the forming pore, which binds with negative phosphate group of ssDNA. Therefore, When the wild type E1-1 (306-577) or E1-2 (306-605) monomer is inserted into the artificial lipid membrane to form an conducting pore through which ions can freely pass it was found that the pore would fall from the lipid membrane at a long period of applied transmembrane voltage. The recorded open current baseline fluctuated, and small non-specific peak current is appeared occasionally when no molecule to be measured passes through the pore.

We use mutated E1-1 (306-577) or E1-2 (306-605) monomer to improve the above defects. For example, some acidic amino acids at the wider C terminal like aspartic acid (D) at 479 and 489 are mutated to histidine (H) or lysine (K) to increase the capture efficiency of negatively charged nucleic acid at the C terminal of the pore. When mutated to asparagine (N), the density of negatively charged amino acids at C-terminal opening decreased, and the electrostatic antagonism to nucleic acids (mainly) or negatively charged substances to be measured is correspondingly reduced, which indirectly increases the capture rate of the pore.

Another example is that we mutate some acidic amino acids in the pore cavity such as aspartic acid (D) at 504, glutamate (E) at 328, to asparagine (N), lysine (K), arginine (R), Glutamine (Q), etc. Mutating acidic amino acids (D, E) to neutral amino acids, on the one hand, can significantly reduce the electrostatic antagonism during nucleic acid translocation, on the other hand, When the neutral amino acid is phenylalanine (F), tryptophan (W), or tyrosine (Y) with a large steric hindrance, due to the larger spatial position within the formed cavity, the diameter of the non-restricted site in the cavity is significantly reduced. At the same time, when the density of benzene ring inside the substituted cavity increases, π electrons accumulate to make amino acids align more closely and the internal contraction of the cavity is obvious. Of course, these two reductions are double-edged swords in detection. When the neutral amino acid is a hydroxyl group, such as serine (S) or threonine (T), because hydroxyl oxygen can bond with nucleotides by forming hydrogen, the nucleic acid is able to enter the cavity from the C terminal to translocate more slowly. This mechanism will have more beneficial value in the subsequent development of nucleic acid sequencing.

Mutating aspartic acid (D) at 322, 342, 334, glutamate (E) at 372, lysine (K) at 396, 383, histidine (H) at 323 and arginine (R) at 574 in the transmembrane region to neutral amino acid Leucine (L), Glycine (G), alanine (A), etc. enable transmembrane region of the pore more easily and stably embed in the hydrophobic layer of lipid bilayer composed of long fatty acid chains, thus greatly weaken the open current baseline fluctuations and low frequency noise caused by instability of pore inserting. The specific mutation site is shown in table 3 below.

TABLE 3

| Mutant sites | | |
|---|---|---|
| location | substitution | advantage |
| D479 | H | The antagonism of DNA decreases |
| D479 | K | The capture of DNA improves |
| D479 | S | Pore is stable |
| D479 | N | The antagonism of DNA decreases |
| D479 | T | Pore is stable |
| D489 | H | The antagonism of DNA decreases |
| D489 | K | The capture of DNA improves |
| D489 | N | The antagonism of DNA decreases |
| D489 | T | Pore is stable |
| D489 | S | Pore is stable |
| D530 | H | The antagonism of DNA decreases |
| D530 | K | The capture of DNA improves |
| D530 | N | The antagonism of DNA decreases |
| D530 | T | Pore is stable |
| D530 | S | Pore is stable |
| D529 | H | Pore is stable |
| D529 | K | The capture of DNA improves |
| D525 | H | Pore is stable |
| D525 | K | The capture of DNA improves |
| D525 | N | The antagonism of DNA decreases |
| D525 | T | Pore is stable |
| D525 | S | Pore is stable |
| D504 | N | DNA transports easily, the signal to noise ratio improves |
| D504 | K | DNA transports easily |
| D504 | R | DNA transports easily |
| D504 | Y | Hydrogen bonding, more compact cavity |
| D504 | S | Hydrogen bonding |

TABLE 3-continued

| Mutant sites | | |
|---|---|---|
| location | substitution | advantage |
| D504 | T | Hydrogen bonding |
| E328 | H | DNA transports easily, the signal to noise ratio improves |
| E328 | K | DNA transports easily |
| E328 | R | DNA transports easily |
| E328 | S | Hydrogen bonding |
| E328 | T | Hydrogen bonding |
| E328 | W | More compact cavity |
| E328 | F | More compact cavity |
| E328 | Y | More compact cavity, hydrogen bonding, detection range and sensitivity increase |
| D360 | N | DNA transports easily, the signal to noise ratio improves |
| D360 | K | DNA transports easily |
| D360 | R | DNA transports easily |
| D360 | S | Hydrogen bonding |
| D360 | T | Hydrogen bonding |
| D360 | W | More compact cavity |
| D360 | F | More compact cavity |
| D360 | Y | More compact cavity, hydrogen bonding, detection range and sensitivity increase |
| D322 | N | Pore is stable, the signal to noise ratio improves |
| D322 | L | Pore is stable, the signal to noise ratio improves |
| D322 | I | Pore is stable, the signal to noise ratio improves |
| D322 | V | Pore is stable |
| D322 | F | Pore is stable |
| D322 | W | Pore is stable, the signal to noise ratio improves |
| D322 | H | Pore is stable, the signal to noise ratio improves |
| E372 | H | Pore is stable |
| E372 | L | Pore is stable, the signal to noise ratio improves |
| E372 | I | Pore is stable, the signal to noise ratio improves |
| E372 | V | Pore is stable |
| E372 | P | Pore is stable |
| E372 | F | Pore is stable, the signal to noise ratio improves |
| E372 | W | Pore is stable, the signal to noise ratio improves |
| E372 | N | Pore is stable |
| D342 | N | Pore is stable |
| D342 | L | Pore is stable, the signal to noise ratio improves |
| D342 | I | Pore is stable |
| D342 | V | Pore is stable |
| D342 | F | Pore is stable, the signal to noise ratio improves |
| D342 | W | Pore is stable, the signal to noise ratio improves, the opening current level is stable |
| D342 | H | Pore is stable |
| D334 | N | Pore is stable |
| D334 | L | Pore is stable, the signal to noise ratio improves |
| D334 | I | Pore is stable |
| D334 | V | Pore is stable |
| D334 | F | Pore is stable, the signal to noise ratio improves, the opening current level is stable |
| D334 | W | Pore is stable, the signal to noise ratio improves, the opening current level is stable |
| D334 | H | Pore is stable |
| D392 | N | Pore is stable |
| D392 | L | Pore is stable, the signal to noise ratio improves |
| D392 | I | Pore is stable |
| D392 | V | Pore is stable |
| D392 | F | Pore is stable |
| D392 | W | Pore is stable, the opening current level is stable |
| D392 | H | Pore is stable |
| D408 | N | Pore is stable |
| D408 | L | Pore is stable, the signal to noise ratio improves |
| D408 | I | Pore is stable |
| D408 | V | Pore is stable |
| D408 | F | Pore is stable, the signal to noise ratio improves |
| D408 | W | Pore is stable, the signal to noise ratio improves |
| D408 | H | Pore is stable |
| K396 | L | Pore is stable |
| K396 | I | Pore is stable |
| K396 | V | Pore is stable |
| K396 | F | Pore is stable, the signal to noise ratio improves |
| K396 | W | Pore is stable, the signal to noise ratio improves, the opening current level is stable |
| K396 | A | Pore is stable |
| K396 | G | Pore is stable |
| R570 | V | Pore is stable |

TABLE 3-continued

| location | substitution | advantage |
|---|---|---|
| R570 | F | Pore is stable, the signal to noise ratio improves, the opening current level is stable |
| R570 | W | Pore is stable, the signal to noise ratio improves |
| R570 | A | Pore is stable |
| R570 | G | Pore is stable |
| R570 | L | Pore is stable, the signal to noise ratio improves |
| R570 | I | Pore is stable |
| R574 | F | Pore is stable, the signal to noise ratio improves, the opening current level is stable |
| R574 | W | Pore is stable, the signal to noise ratio improves |
| R574 | A | Pore is stable |
| R574 | G | Pore is stable |
| R574 | L | Pore is stable, the signal to noise ratio improves |
| R574 | I | Pore is stable |
| R574 | V | Pore is stable |
| K417 | L | Pore is stable, the signal to noise ratio improves |
| K417 | I | Pore is stable |
| K417 | V | Pore is stable |
| K417 | F | Pore is stable, the signal to noise ratio improves |
| K417 | W | Pore is stable, the signal to noise ratio improves, the opening current level is stable |
| K417 | A | Pore is stable |
| K417 | G | Pore is stable |
| K421 | V | Pore is stable |
| K421 | F | Pore is stable, the signal to noise ratio improves, the opening current level is stable |
| K421 | W | Pore is stable, the signal to noise ratio improves, the opening current level is stable |
| K421 | A | Pore is stable |
| K421 | G | Pore is stable |
| K421 | L | Pore is stable, the signal to noise ratio improves |
| K421 | I | Pore is stable, the signal to noise ratio improves |
| K383 | V | Pore is stable |
| K383 | F | Pore is stable, the signal to noise ratio improves |
| K383 | A | Pore is stable |
| K383 | G | Pore is stable |
| K383 | L | Pore is stable, the signal to noise ratio improves |
| K383 | I | Pore is stable, the signal to noise ratio improves |
| K383 | W | Pore is stable, the signal to noise ratio improves, the opening current level is stable |
| K387 | H | Pore is stable, the signal to noise ratio improves |
| K387 | F | Pore is stable, the signal to noise ratio improves, the opening current level is stable |
| K387 | W | Pore is stable, the signal to noise ratio improves, the opening current level is stable |
| H323 | L | Pore is stable, the signal to noise ratio improves |
| H323 | I | Pore is stable, the signal to noise ratio improves |
| H323 | V | Pore is stable |
| H323 | F | Pore is stable, the signal to noise ratio improves, the opening current level is stable |
| H323 | W | Pore is stable, the signal to noise ratio improves, the opening current level is stable |
| H323 | A | Pore is stable |
| H323 | G | Pore is stable |
| K324 | L | Pore is stable, the signal to noise ratio improves |
| K324 | I | Pore is stable, the signal to noise ratio improves |
| K324 | P | Pore is stable, the signal to noise ratio improves, the opening current level is stable |
| K324 | V | Pore is stable |
| K565 | T | Pore is stable |
| K565 | S | Pore is stable |
| K565 | Y | Pore is stable |
| K426 | L | Pore is stable, the signal to noise ratio improves |
| K426 | I | Pore is stable, the signal to noise ratio improves |
| K426 | V | Pore is stable |
| K426 | F | Pore is stable, the signal to noise ratio improves, the opening current level is stable |
| K426 | W | Pore is stable, the signal to noise ratio improves, the opening current level is stable |
| K426 | A | Pore is stable |
| K426 | G | Pore is stable |

The present invention is further elaborated by embodiments as follows.

Embodiment 1 Construction and Expression Purification of E1 Protein and its Mutant Recombinant Vector The amino acid sequence (SEQ ID No. 3) of truncated E1-1 (306-577):
LQTEKFDFGTMVQWAYDHKYAEESKIAYEYALAAGSDSNARAFLAT

NSQAKHVKDCATMVRHYLRAETQALSMPAYIKARCKLATGEGSWKSILTFF

NYQNIELITFINALKLWLKGIPKKNCLAFIGPPNTGKSMLCNSLIHFLGGSVLSF

ANHKSHFWLASLADTRAALVDDATHACWRYFDTYLRNALDGYPVSIDRKH

KAAVQIKAPPLLVTSNIDVQAEDRYLYLHSRVQTFRFEQPCTDESGEQPFNIT

DADWKSFFVRLWGRLDL.

The coding gene sequence (SEQ ID No. 4) of the truncated E1-1 (306-577):
Ttgcagaccgagaaattcgacttcggaactatggtgcaatgggcctatgatcacaaatatgctgaggagtctaa aatagcctatgaatatgctttggctgcaggatctgatagcaatgcacgggctttttttagcaactaacagccaagctaagcatgt gaaggactgtgcaactatggtaagacactatctaagagctgaaacacaagcattaagcatgcctgcatatattaaagctagg tgcaagctggcaactggggaaggaagctggaagtctatcctaactttttttaactatcagaatattgaattaattacctttattaat gattaaagctctggctaaaaggaattccaaaaaaaaactgtttagcatttattggccctccaaacacaggcaagtctatgctc tgcaactcattaattcatttttgggtggtagtgttttatcttttgccaaccataaaagtcacttttggcttgcttccctagcagatac tagagctgctttagtagatgatgctactcatgcttgctggaggtactttgacacatacctcagaaatgcattggatggctaccct gtcagtattgatagaaaacacaaagcagcggttcaaattaaagctccacccctcctggtaaccagtaatattgatgtgcagg cagaggacagatatttgtacttgcatagtcgggtgcaaacctttcgctttgagcagccatgcacagatgaatcgggtgagca accttttaatattactgatgcagattggaaatcttttttgtaaggttatgggggcgtttagacctg.

Vector plasmid: pGEX-6p-1.

Double digestion: BamH I, Xho I.

Primer (lowercase letters are restriction sites):
Forward primer: SEQ ID No. 10;
CGggatccTTGCAGACCGAGAAAT.

Reverse primer: SEQ ID No. 11
CCGctcgagTTAATGATGATGGTGATGATGCAGGTCTAAACGCCCC.

The amino acid sequence (SEQ ID No. 1) of truncated E1-2 (306-605):
LQTEKFDFGTMVQWAYDHKYAEESKIAYEYALAAGSDSNARAFLAT

NSQAKHVKDCAMVRHYLRAETQALSMPAYIKARCKLATGEGSWKSILTFFN

YQNIELITFINALKLWLKGIPKKNCLAFIGPPNTGKSMLCNSLIHFLGGSVLSFA

NHKSHFWLASLADTRAALVDDATHACWRYFDTYLRNALDGYPVSIDRKHK

AAVQIKAPPLLVTSNIDVQAEDRYLYLHSRVQTFRFEQPCTDESGEQPFNITD

ADWKSFFVRLWGRLDLIDEEEDSEEDGDSMRTFTCSARNTNAVD.

The coding gene sequence (SEQ ID No. 2) of the truncated E1-2 (306-605):
ttgcagaccgagaaattcgacttcggaactatggtgcaatgggcctatgatcacaaatatgctgaagagtctaaa atagcctatgaatatgctttggctgcaggatctgatagcaatgcacgggctttttagcaactaacagccaagctaagcatgtg aaggactgtgcaactatggtaagacactatctaagagctgaaacacaagcattaagcatgcctgcatatattaaagctaggt gcaagctggcaactggggaaggaagctggaagtctattctaactttttttaattatcagaatattgaattaattacctttattaatg ctttaaagctctggctaaaaggaattccaaaaaaaaactgtttagcatttattggccctccaaacacaggcaagtctatgctct gcaactcattaattcattttttggtggtagtgttttatcttttgccaaccataaaagtcacttttggcttgcttccctagcagatact agagctgctttagtagatgatgctactcatgcttgctggaggtactttgacacatacctcagaaatgcattggatggctaccct gtcagtattgatagaaaacacaaagcagcggttcaaattaaagctccacccctcctggtaaccagtaatattgatgtgcagg cagaggacagatatttgtacttgcatagtcgggtgcaaacctttcgctttgagcagccatgcacagatgaatcgggtgagca accttttaatattactgatgcagattggaaatcttttttgtaaggttatgggggcgtttagacctgattgacgaggaggaggata gtgaagaggatggagacagcatgcgaacgtttacatgtagcgcaagaaacacaaatgcagttgattga.

Vector plasmid: pGEX-6p-1.

Double digestion: BamH I, Xho I.

Primer (lowercase letters are restriction sites):
Forward primer 1: SEQ ID No. 12
AGTTCTGTTCCAGGGGCCCCTGggatccTTGCAGACCGAGAAATTCGA

CTTCG.

Reverse primer 1: SEQ ID No. 13
TCAGTCAGTCACGATGCGGCCGctcgagTTAATCAACTGCATTTGTGTT

TCTTGCGCTACATGTAAACGTTCGCA.

The amino acid sequence of E1-2 mutant 1 (K421L) is shown in SEQ ID No. 6:
LQTEKFDFGTMVQWAYDHKYAEESKIAYEYALAAGSDSNARAFLATN

SQAKHVKDCATMVRHYLRAETQALSMPAYIKARCKLATGEGSWKSILTFFNY

QNIELITFINALKLWLLGIPKKNCLAFIGPPNTGKSMLCNSLIHFLGGSVLSFAN

HKSHFWLASLADTRAALVDDATHACWRYFDTYLRNALDGYPVSIDRKHKAA

VQIKAPPLLVTSNIDVQAEDRYLYLHSRVQTFRFEQPCTDESGEQPFNITDADW

KSFFVRLWGRLDLIDEEEDSEEDGDSMRTFTCSARNTNAVD.

-continued

The nucleotide sequence of E1-2 mutant 1 is shown in SEQ ID No. 8:
GGATCCTTGCAGACCGAGAAATTCGACTTCGGAACTATGGTGCAAT

GGGCCTATGATCACAAATATGCTGAGGAGTCTAAAATAGCCTATGAATATGC

TTTGGCTGCAGGATCTGATAGCAATGCACGGGCTTTTTTAGCAACTAACAG

CCAAGCTAAGCATGTGAAGGACTGTGCAACTATGGTAAGACACTATCTAAG

AGCTGAAACACAAGCATTAAGCATGCCTGCATATATTAAAGCTAGGTGCAA

GCTGGCAACTGGGGAAGGAAGCTGGAAGTCTATCCTAACTTTTTTTAACTA

TCAGAATATTGAATTAATTACCTTTATTAATGCTTTAAAGCTCTGGCTACTGG

GAATTCCAAAAAAAAACTGTTTAGCATTTATTGGCCCTCCAAACACAGGCA

AGTCTATGCTCTGCAACTCATTAATTCATTTTTTGGGTGGTAGTGTTTTATCT

TTTGCCAACCATAAAAGTCACTTTTGGCTTGCTTCCCTAGCAGATACTAGAG

CTGCTTTAGTAGATGATGCTACTCATGCTTGCTGGAGGTACTTTGACACATA

CCTCAGAAATGCATTGGATGGCTACCCTGTCAGTATTGATAGAAAACACAA

AGCAGCGGTTCAAATTAAAGCTCCACCCCTCCTGGTAACCAGTAATATTGAT

GTGCAGGCAGAGGACAGATATTTGTACTTGCATAGTCGGGTGCAAACCTTT

CGCTTTGAGCAGCCATGCACAGATGAATCGGGTGAGCAACCTTTTAATATTA

CTGATGCAGATTGGAAATCTTTTTTTGTAAGGTTATGGGGGCGTTTAGACCT

GATTGACGAGGAGGAGGATAGTGAAGAGGATGGAGACAGCATGCGAACGT

TTACATGTAGCGCAAGAAACACAAATGCAGTTGATTAACTCGAG.

The amino acid sequence of E1-2 mutant 2 (H323W) is shown in SEQ ID No. 7:
LQTEKFDFGTMVQWAYDWKYAEESKIAYEYALAAGSDSNARAFLATN

SQAKHVKDCATMVRHYLRAETQALSMPAYIKARCKLATGEGSWKSILTFFNY

QNIELITFINALKLWLLGIPKKNCLAFIGPPNTGKSMLCNSLIHFLGGSVLSFAN

HKSHFWLASLADTRAALVDDATHACWRYFDTYLRNALDGYPVSIDRKHKAA

VQIKAPPLLVTSNIDVQAEDRYLYLHSRVQTFRFEQPCTDESGEQPFNITDADW

KSFFVRLWGRLDLIDEEEDSEEDGDSMRTFTCSARNTNAVD.

The nucleotide sequence of E1-2 mutant 2 is shown in SEQ ID No. 9:
GGATCCTTGCAGACCGAGAAATTCGACTTCGGAACTATGGTGCAAT

GGGCCTATGATTGGAAATATGCTGAGGAGTCTAAAATAGCCTATGAATATGC

TTTGGCTGCAGGATCTGATAGCAATGCACGGGCTTTTTTAGCAACTAACAG

CCAAGCTAAGCATGTGAAGGACTGTGCAACTATGGTAAGACACTATCTAAG

AGCTGAAACACAAGCATTAAGCATGCCTGCATATATTAAAGCTAGGTGCAA

GCTGGCAACTGGGGAAGGAAGCTGGAAGTCTATCCTAACTTTTTTTAACTA

TCAGAATATTGAATTAATTACCTTTATTAATGCTTTAAAGCTCTGGCTAGGAA

TTCCAAAAAAAAACTGTTTAGCATTTATTGGCCCTCCAAACACAGGCAAGT

CTATGCTCTGCAACTCATTAATTCATTTTTTGGGTGGTAGTGTTTTATCTTTT

GCCAACCATAAAAGTCACTTTTGGCTTGCTTCCCTAGCAGATACTAGAGCT

GCTTTAGTAGATGATGCTACTCATGCTTGCTGGAGGTACTTTGACACATACC

TCAGAAATGCATTGGATGGCTACCCTGTCAGTATTGATAGAAAACACAAAG

CAGCGGTTCAAATTAAAGCTCCACCCCTCCTGGTAACCAGTAATATTGATGT

GCAGGCAGAGGACAGATATTTGTACTTGCATAGTCGGGTGCAAACCTTTCG

CTTTGAGCAGCCATGCACAGATGAATCGGGTGAGCAACCTTTTAATATTACT

-continued

```
GATGCAGATTGGAAATCTTTTTTTGTAAGGTTATGGGGGCGTTTAGACCTGA

TTGACGAGGAGGAGGATAGTGAAGAGGATGGAGACAGCATGCGAACGTTT

ACATGTAGCGCAAGAAACACAAATGCAGTTGATTAACTCGAG.
```

A mutant recombinant plasmid is constructed, and the mutated vector inserts
into the vector plasmid pGEX-6P-1 by PCR cloning, and the double restriction sites
are 5'BamhI and 3'XhoI respectively.

Forward primer 2: SEQ ID No. 14
```
AGTTCTGTTCCAGGGGCCCCTGggatccTTGCAGACCGAGAAATTCGA

CTTCG.
```

Reverse primer 2: SEQ ID No. 15
```
TCAGTCAGTCACGATGCGGCCGctcgagTTAATCAACTGCATTTGTGTT

TCTTGCGCTACATGTAAACGTTCGCA.
```

The entire bovine papillomavirus genome is amplified using the above PCR primers (as described above), and then the vector pGEX-6p-1 and the resulting PCR product are digested with two restriction enzymes BamH I and Xho I. The vector carried the GST-tag affinity containing two restriction sites of BamH I and Xho I respectively. Finally, the double-digested target gene fragment and the plasmid vector are religated into a circular recombinant plasmid by T4 ligase.

The detection of recombinant plasmid is to preliminarily screen whether the recombinant plasmid is successfully transformed or not by using ampicillin resistance of the recombinant vector after the transformed plasmid into *E. coli* DH5a. After colony PCR, the nucleic acid gel electrophoresis is used to preliminarily verify whether the target fragment is ligated into the vector (as shown in FIG. 1, pGEX-6p-1 is 4984 bp in length, and the E1-1 gene sequence is 816 bp in length, so two bands are obtained after digestion, respectively 4990 bp and 822 bp). Then sequencing results obtained by the gene sequencing are used to confirm whether the recombination is completed and no mutation occurs.

The specific expression and purification of E1 protein: recombinant plasmid pGEX-6p-1-N-GST is transformed into *E. coli* expression strain BL21 for protein expression. The above *E. coli* is cultured overnight in 11 mL LB medium containing 50 μg/mL ampicillin at 37° C. and 220 rpm. Then, 10 mL of culture solution is injected into 1 L of fresh LB medium containing 50 μg/ml ampicillin, and 0.5 mM (final concentration) IPTG (Isopropyl β-D-Thiogalactoside) is added to induct when the bacterial concentration reaches 0.6-0.8 units ($OD_{600}$). After induction for 16 hours at 16° C., the bacteria are harvested by centrifugation at 4000 rpm for 20 minutes, and the suspension is resuspended in protein buffer 20 mM tris-HCl (pH 7.3), 200 mM NaCl. After the bacteria are broken by high pressure four times, the supernatant is harvested by centrifugation at 16000 rpm for 40 minutes. Then the supernatant is filtered through a 0.45 μm pore size filter and the target protein is purified by GST affinity chromatography. After the hybrid protein is eluted, the target protein is digested on the PSP enzyme column for 2 hours, and then the target protein is elute with protein buffer.

Figure 2:
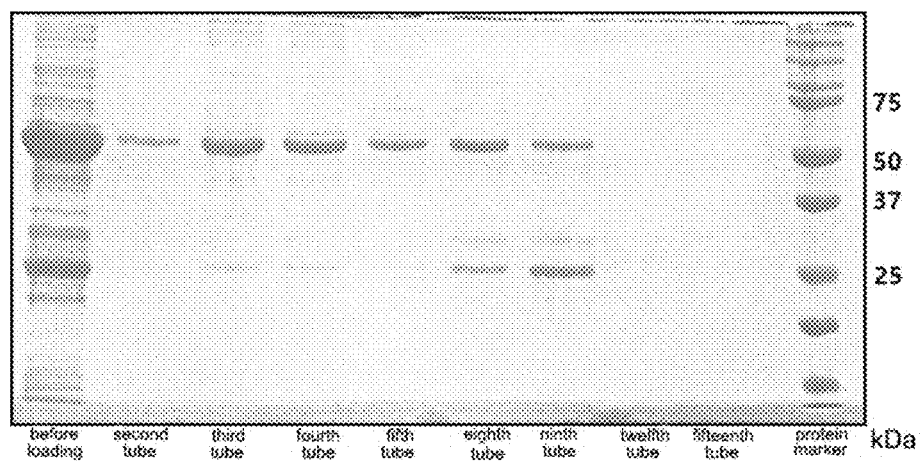
FIG. 2: The target protein in each peak was detected by polyacrylamide gel electrophoresis after the hybrids of E1-1 (306-577) protein monomer (57 KD) passed through molecular sieve. The second tube was used in the subsequent electrophysiological experiments.
Figure 3:
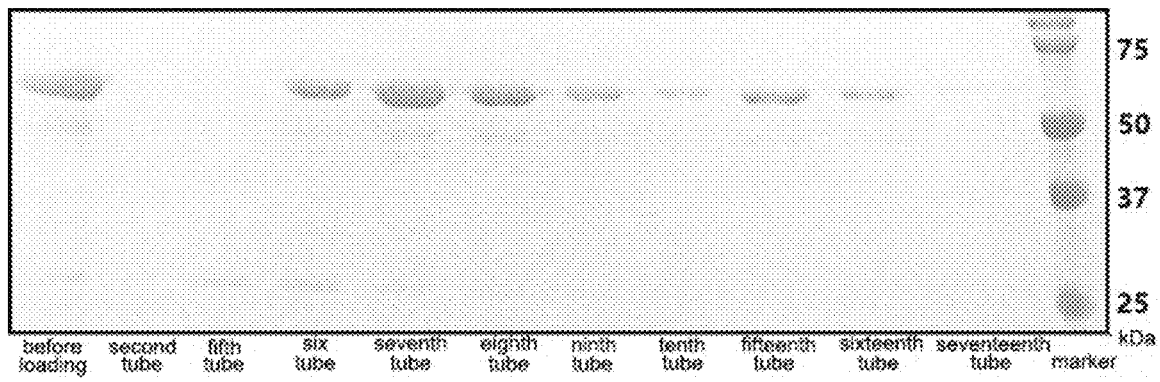
FIG. 3: The target protein in each peak was detected by polyacrylamide gel electrophoresis after the hybrids of E1-1 (306-605) protein monomer (59 KD) passed through molecular sieve. The sixth tube was used in the subsequent electrophysiological experiments.
Figure 4:
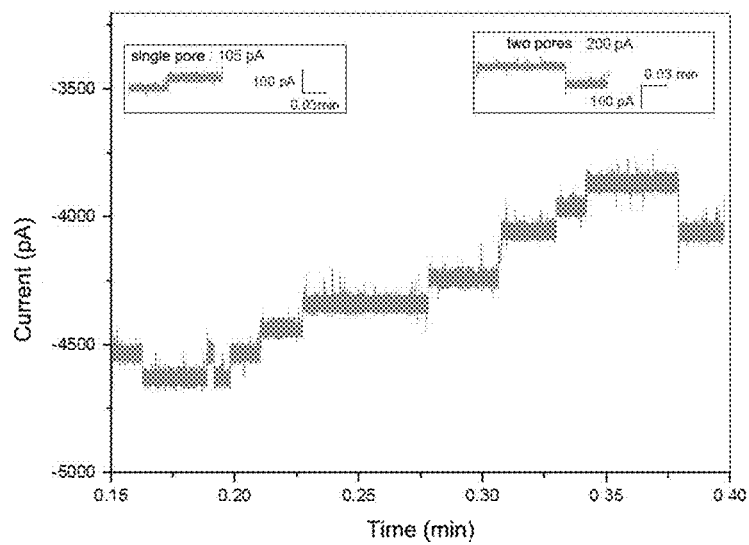
FIG. 4: At 70 mV transmembrane voltage, the current of a single-pore is about 105 pA, and that of a double-pore is around 200 pA.
Figure 5:
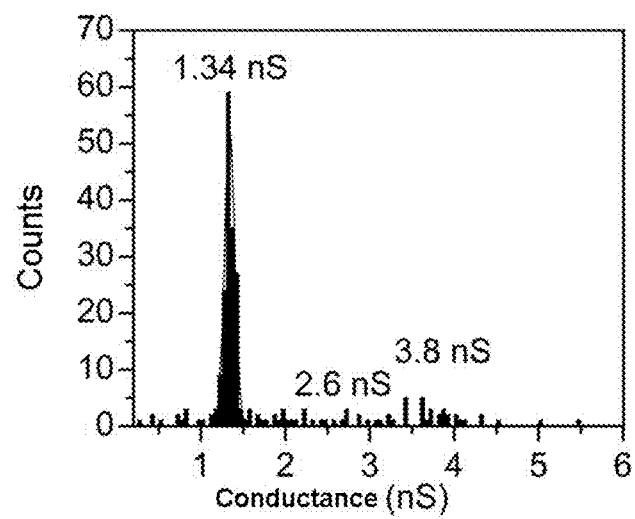
FIG. 5: The single-pore conductance distribution is around 1.3±0.07 nS by analyzing a large number of pore currents.
Figure 6:
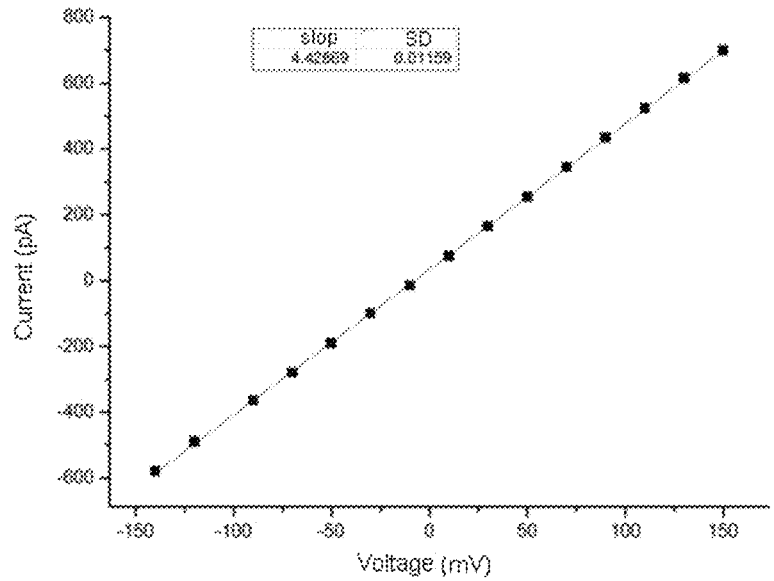
FIG. 6: The slope of the I-V curve obtained at the slope voltage is about 4.43 (four pores), so the single-pore conductance is about 1.5.
Figure 7:
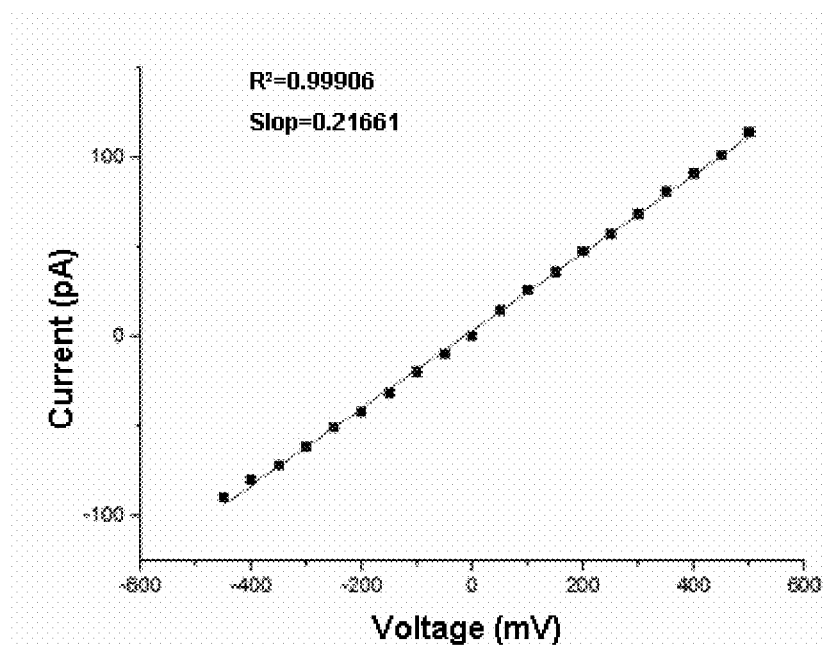
FIG. 7: When using PBS as the conductivity buffer, the conductance distribution of the protein is 0.2±0.02 nS, and the current of single-pore is about 23 pA at a voltage of −70 mV.

The purity of the target protein is high after purification by GST affinity chromatography. Finally, the molecular sieve is used to separate the polymer and the monomer, and the first peak protein is the pure E1. Simultaneously, from the analysis of the peak position of molecular sieve, the obtained E1 is in the form of hexamer, and the wild E1 form is very similar. The remaining protein samples are tested by polyacrylamide gel electrophoresis to meet the expected size. FIGS. 2 and 3 are the polyacrylamide gel electrophoresis patterns of the molecular sieve peaks of E1-1 and E1-2 respectively. The corresponding monomer molecular weights are 57 KD and 59 KD respectively. The second tube (E1-1) and the sixth tube (E1-2) are used in the subsequent electrophysiological experiments.

Figure 21:
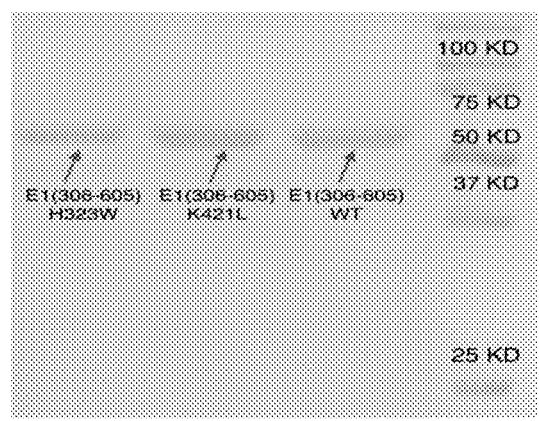
FIG. 21: E1-1 (306-605, K421L, H323W) protein monomer (59 KD) and WT-E1 (306-605) proteins were detected by polyacrylamide gel electrophoresis respectively.
Figure 22:
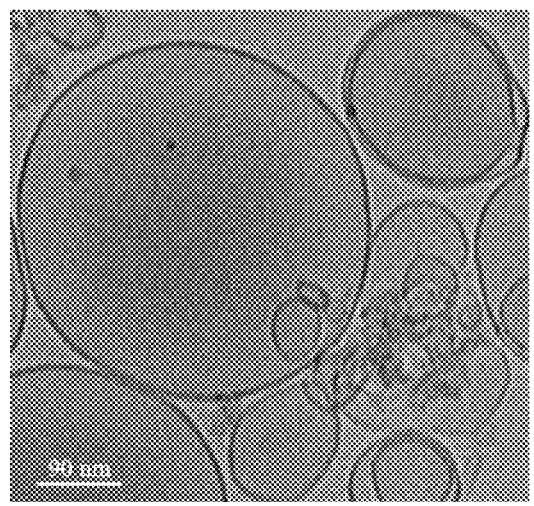
FIG. 22, 23: The electron micrograph of mutant E1 (306-605, K421L, H323W) embedded in giant lipid vesicle membrane (Tabs F200C, scale 90 nm) is shown in FIG. 22; The electron micrograph of mutant E1 (306-605, K421L, H323W) embedded in giant lipid vesicle membrane (Tabs F200C, scale 90 nm) is shown in FIG. 23.
Figure 23:
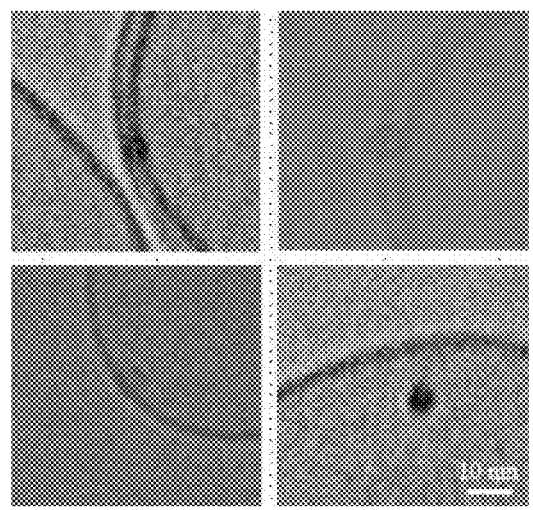
Figure 24:
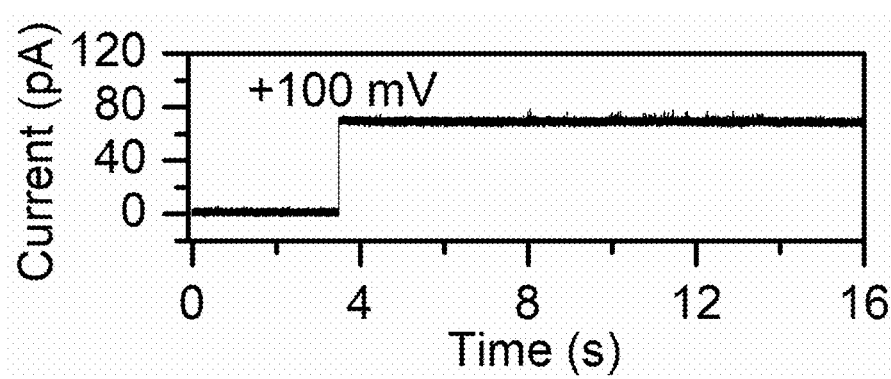
FIG. 24: Single-pore embedding of hexamer E1-1 (306-605, K421L, H323W) protein induces a transient rise in current of approximately 75 pA at 100 mV in 0.5 M KCl, 10 mM Hepes (pH 7.5) conductivity buffer.

The methods for gene cloning and expression purification of two mutants refers to wild type E1 (306-605), and the first appeared peak-tube after molecular sieve collection is the mutant E1. The remaining protein samples are tested by polyacrylamide gel electrophoresis compared with WT-E1 (306-605), since only one amino acid is mutated, the molecular weight of the mutant is very close to the WT-E1 (306-605) protein. Moreover, they are almost in a same position on the gel electrophoresis strip, as shown in FIG. 21.

Embodiment Two, Fluorescent Labeling and Membrane Fusion Experiments of Protein Truncations and their Mutants Fluorescently labeled truncated E1-2 (306-605) protein: The material used is a fluorine-labeled fluorescein isothiocyanate (FITC) conjugate kit (Sigma, St. Louis, Missouri). According to the kit description, the excess FITC is removed by column chromatography, and the FITC-linked E1 is eluted with protein buffer (20 mM tris-HCl (pH7.3), 200 mM NaCl). Verified FITC labels E1 (306-605) with SDS-PAGE (Figure omitted, the position of FITC labeled E1-2 on SDS-PAGE is slightly higher than that of unlabeled E1-2).

Preparation of vesicles (SUVs) containing truncated bodies E1-2 (306-605): In order to prepare vesicles of about 0.1 um in size containing E1 protein, 1 mg/mL of DOPC is add into a vial. The aqueous solution containing protein E1 (concentration about 0.5 mg/ml) is added after nitrogen blow dry the chloroform, then hydrates the lipid membrane to make suspension, and this suspension is further extruded by Mini squeezer (purchased from AVANTI Co. Ltd, America) through polycarbonate (PC) films (diameter of 100 nm) to produce protein-SUVs. The resulted SUVs can be stored at 4° C. for a short term and at −80° C. for a long term; Only the SUVs without labeled by fluorescence shows similar form to vesicles of the same size under optical microscope. (The resulted protein-SUVs by Mini squeezer have a good uniformity).

The procedure of preparing giant vesicles containing truncated E1-2 (306-605): meanwhile, giant vesicles labeled with fluorescence could also be prepared. Mixing 1 ml of DOPC (1 mg/ml) or 1 ml of DPHPC (1 mg/ml) and 1% of Texas Red (purchased from Thermofisher Co. Ltd, America) in a brown bottle; then drying chloroform by nitrogen, or volatilizing chloroform in rotary evaporator in this procedure; next, putting DOPC or DPHPC obtained from above step in vacuum drier overnight; In order to acquire hybrid giant unilamellar vesicles (GUVs) inserted E1 protein, adding 200-300 Mm of sucrose solution which containing E1 (concentration about 0.5 mg/ml) to hydrate the lipid molecular layer.

Those vesicles labeled with Texas Red can be observed in fluorescence microscope. To prepare fluorescence-labeled protein complexes embedded with vesicles, FITC-labeled E1-2 obtained from previous procedure can be used here. The result of observing GUVs in fluorescence microscope shows that the size of vesicles with larger diameter obtained by rotary evaporator is not as uniform as that of SUVs prepared by squeezer. Some vesicle protein complex with diameter over 50 μm are found in latter nanopore insertion with artificial membrane trail, and these vesicles easily ruptures bilayer lipid membrane (artificial lipid membrane is formed on the surface of 50 μm-diameter hole which made up of polyacetal resin, purchased from Warner Co. Ltd, America).

Conducting membrane fusion experiment on the mutant of truncated E1-2 with the same method, the result shows that, consistent with WT-E1 (306-605), this protein can also be steady inserted into the artificial lipid bilayer and PMOXA-PDMS-PMOXA triblock copolymer. The procedure of the experiment is similar to that of WT-E1 (306-605), when the GUVs inserted with mutant E1 is obtained, the protein embedding on the membrane is observed by Cryo-EM, and as shown in FIG. 22 and FIG. 23, the porin can steady exist on the membrane.

The double-labeled vesicle-embedded protein complex (red as the Texas red labeled vesicles, and green as the FITC labeled E1-2 protein) is observed under fluorescence microscope, and it is found that some labeled E1-2 protein shows irregular positioning on vesicle membrane, part of the "transmembrane region" as expected is inserted into the phospholipid bilayer to form pores. This result also proves that in the conductance buffer, E1-2 can spontaneously aggregate on the artificial lipid membrane driven by voltage and can insert into the membrane in an expected direction to form a conductive pore.

Embodiment Three, the Electrophysiological Experiment of E1 Protein and its Mutant Electrophysiological measurement: the instrument used in this embodiment is HEKA EPC-10 USB which integrates Amplifier and Digital-to-analog converter (DAC), and it has two electrodes named of pressure (voltage clamp) electrode and reference electrode, which are a pair of silver/silver chloride electrodes (Ag/AgCl). The instrument is used to measure the transmembrane current across both sides of the phospholipid bilayer. The sample frequency setup here is 2 kHz, and the frequency of low-pass filter is 1 kHz; the software Patch-master is used to collect the data, and Clampfit is utilized to analyze the collected data.

The fabrication of bilayer lipid membrane (BLM): The horizontal standard BLM fabricator and vertical standard BLM chamber (BCH-13A, purchased from Warner. Co. Ltd, America; Cups contain a 50 μm-diameter hole is custom made) are used to fabricate the BLM. A thin Teflon film with an aperture of 80-240 μm (TP-02 from Eastern Sci. LLC) and a Polyformaldehyde resin CUPS with an aperture of 50 μm are used as a partition to respectively separate BLM fabricator and BLM chamber into cis-compartment (working volume 250 μL) and trans-compartment (working volume 2.5 mL). After the aperture is pre-painted twice with 0.5 μL, 1 mg/ml of DOPC solution or DPHPC solution (the solvent is n-hexane) to ensure the complete coating of the entire edge of the aperture, the two compartments are filled with conducting buffers (5 mM Hepes/pH 7.5, with varying concentration of KCl solution, or PBS solution); Then, adding 25 mg/ml of DOPC solution or DPHPC solution (the solvent is n-hexane) near 50 μm aperture and it finds that the current falling from 10.2 nA to 0 pA.

The distribution of conductance of E1:

The vesicle-protein complex prepared previously forms a BLM embedded with E1-2 protein nanopore structure on the micropores of horizontal ptfe membrane (as described above) or vertical polyformaldehyde resin micropores.

The stock solution of vesicles/E1 complex prepared earlier is diluted by 10-20 times for the BLM experiments before use. For insertion of E1, around 2 μL of the diluted liposome solution is loaded into the cis-chamber; the other simple method is described below: a bubble containing some liposome at the pipette top is used to sweep the aperture gently in the cis-chamber, and the pore would form spontaneously. Conductance of E1 protein is measured in two methods: the first is under a constant transmembrane voltage (e.g. −70 mv), measuring current leap when multiple pores are embedded and dropped, and then counting data to calculate the distribution of conductance of pores. The second method is to apply a scanning voltage (e.g. −120 mv to 120 mv) to both sides of the membrane and calculate the pore conductance by calculating the rate of the current and voltage curve.

In this invention, large numbers of data are counted and the result demonstrates that, the single-pore conductance in 5 mM HEPES and 1 M KCl is around 1.34±0.07 nS (as shown in FIG. 5); The single-pore current level and the two-pores current level are about 105 pA and 200 pA respectively, when given a +70 mV trans-voltage (as shown in FIG. 4). A plot of the I-V curve is obtained under different ramping voltages and the single-pore conductance is measured around 1.5 nS (as shown in FIG. 6). Under the condition of 5 mM HEPES and 0.5M KCl conductance buffer, the measured single-conductance of E1 is around 0.78 ns, at a transmembrane voltage of 50 mv, the current of a single E1 formed pore on the artificial lipid membrane is about 40 pA, and that of double pores is about 85 pA. Under I-V curve, the measured single-pore conductance is about 1.57/2 nS. In PBS as the conductance buffer, the conductance of the protein is 0.2±0.02 nS (as shown in FIG. 7), and the current of single-pore is about 23 pA under a voltage of −70 mV.

The same trial on mutant E1 is conducted, and the result shows that under 0.5 M KCl, 10 Mm HEPES (pH 7.5), single-pore embedding causes about 75 pA of current ascending step when given a +100 mV bias voltage, as shown in FIG. 24, after counting a large number of single-pore embedding and falling signals and under the scanning voltage of −200-200 mv, it is found that the single-pore conductance distribution is similar to that of WT-E1 (306-605) pores, both of which are about 1.3±0.07 nS. Moreover, at the scanning voltage, the scatter linear fitting results of current to voltage are good and the dispersion is low.

Embodiment Four, the Study on the Stability of the Pores of E1 Protein and its Mutant The study on the stability of the pore of E1-2: in this invention, the stability of pores of E1-2 and the mutant of E1 on phospholipids membrane and high voltage-gating phenomenon are studied under positive and negative voltage respectively. The results depicted: no gating phenomenon is found for E1 pore under positive 300 mV and negative 300 mV, and E1 pore could exist on the phospholipids membrane steadily when given a high voltage. At the same time, it is found that when there are too much glycerol in the conductance buffer (used to preserve E1 protein), the membrane embedded protein complex become abnormally unstable, and it is extremely easy for the protein to fall off from the membrane or the membrane to rupture directly.

In the stability experiment of E1 protein mutant (K421L, H323W) at high voltage, the scanning voltage of −300-300 mv is adopted. It finds that at a higher voltage (±300), the pore remained stable on the membrane, and the conductance distribution does not change significantly, showing that the mutant E1 (K421L, H323W) also has stable conductance characteristics as WT-E1 (306-605).

Embodiment Five, Single-Stranded DNA/RNA Translocation Tests of E1 Protein and its Mutant ssDNA used in this embodiment is 48 nt and purchased from Takara company, its detail sequence is depicted as below; The electrolyte is HEPES/1M KCl; In general, there are two methods to achieve nucleic acid transport under this condition.

Method 1: When E1 protein inserts into BLM, changing the voltage to 0 mV and adding the nucleic acids to be transported to the cis; Method 2: the nucleic acid to be transported is pre-mixed into the conductance buffer, and the cis and trans are mixed in the same amount. The translocation of DNA mainly depends on the applied transmembrane voltage. Without special instructions, method 1 is adopted for ssDNA translocation in this experiment, and the concentration of ssDNA in the translocation system is 100 nM/L.

Figure 8:
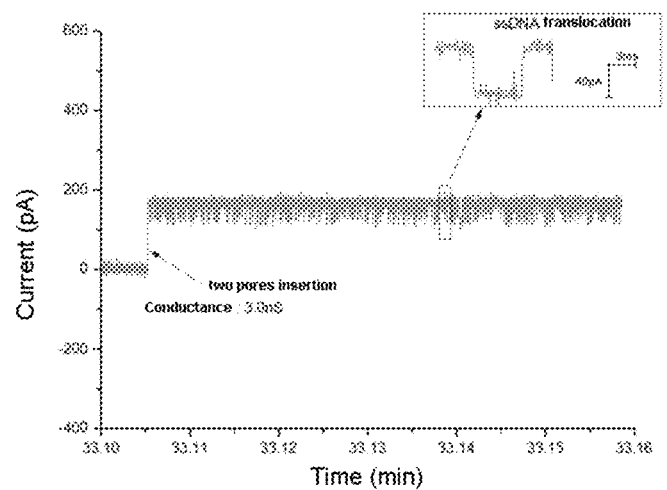
FIG. 8: At 50 mV transmembrane voltage, ssDNA translocation causes a 65 pA blocking current under single-pore condition.
Figure 9:
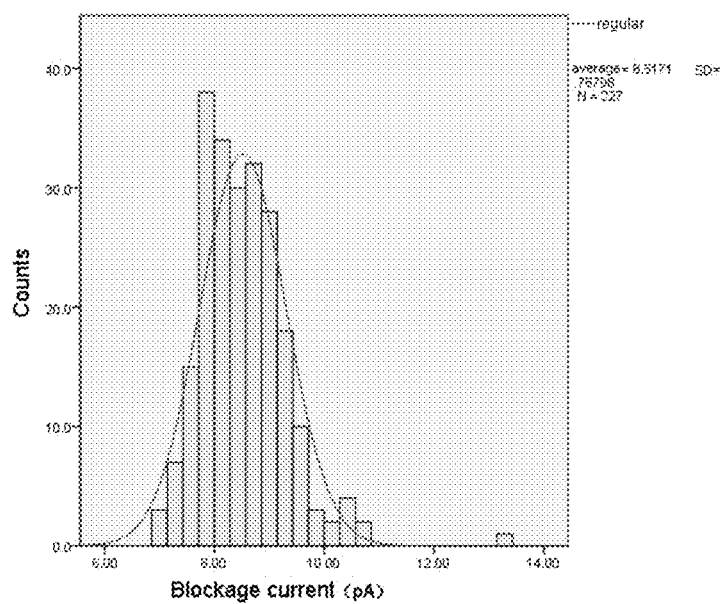
FIG. 9: In the PBS buffer, the blockade of ssRNA translocation in the pore is about 80%, which is similar to KCl buffer.
Figure 10:
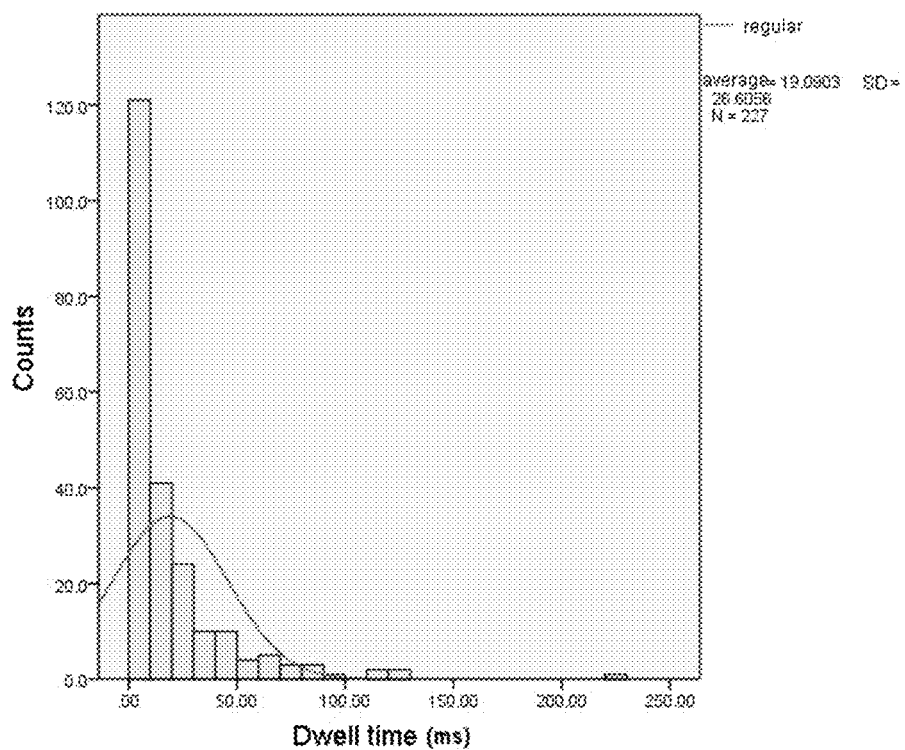
FIG. 10: In the PBS buffer, the blocking current caused by ssRNA is about 8 pA at −50 mV and the translocation time is 1-2 ms.
Figure 29:
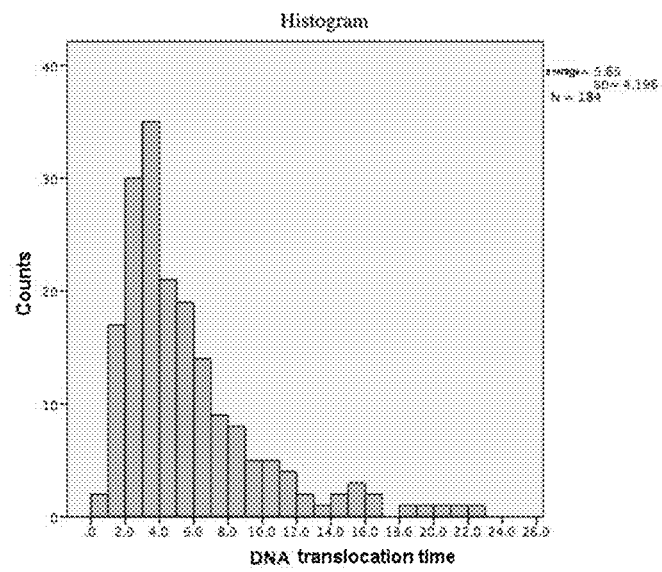
FIG. 29: a histogram of counts against DNA translocation time.
Figure 30:
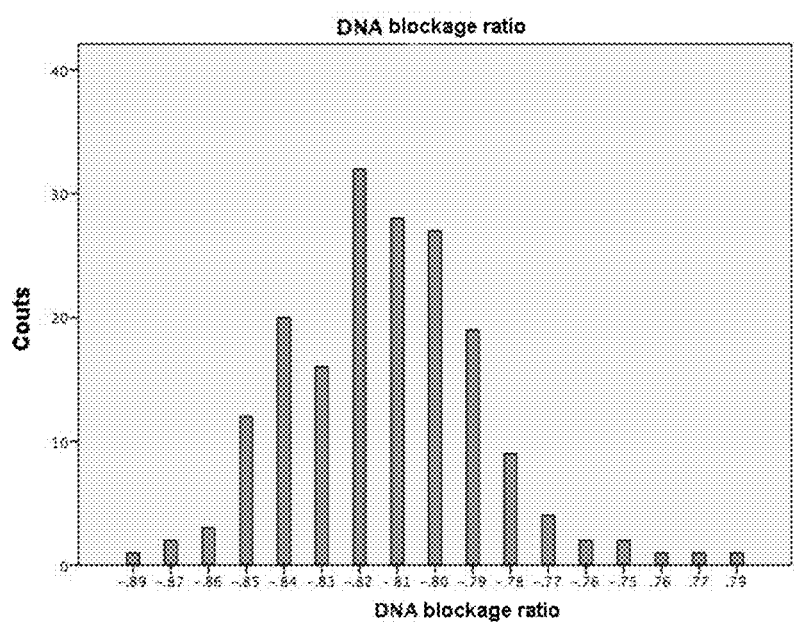
FIG. 30; a graph of counts against DNA blockage ratio.

In the case of the 48 nt ssDNA, the single-pore pore is embedded in the membrane, and the current blocking caused by translocation is about 65 picoamperes (transmembrane voltage is about 50 mv) (as shown in FIG. 8). The current blocking ratio induced by translocation of nucleic acid in this segment is about 82% (Ib/I, Ib is the current blocking caused by nucleic acid translocation, unit is pA; I is the current change caused by the insertion of a single-pore protein into the phospholipid bilayer, unit is pA) The dwell time of ssDNA translocation is 2 ms (as shown in FIGS. 29-30). In PBS, ssDNA translocation experiment shows similar results that under +100 mV transmembrane voltage, 24 nt ssDNA would induced around 80% blockage and 1-2 ms dwell time (as shown in FIGS. 9-10).

Meanwhile, ssRNA translocation experiment is conducted like the ssDNA translocation experiment mentioned above. Noted that using DEPC solution and autoclave sterilization to prevent RNA degradation. The result shows that, similar to ssDNA translocation, ssRNA induced around 80% blockage, and under −50 mV the blocked current in PBS buffer system is about 8 pA, the dwell time is 1-2 ms.

As a comparison, the current trace in the system without nucleic acid but with only pores are static. One advantage of this pore is that the static current in the control group rarely interferes with the non-specific blocking. In the experiment, when nucleic acid premixed into the conductance buffer, amounts of translocation instantly found after the first insertion of the protein pore into the phospholipid membrane, and the blocking phenomenon becomes less and less. This result shows that when there is no stirring equipment in the sample tank, the occurrence of DNA translocation is delayed.

Figure 25:
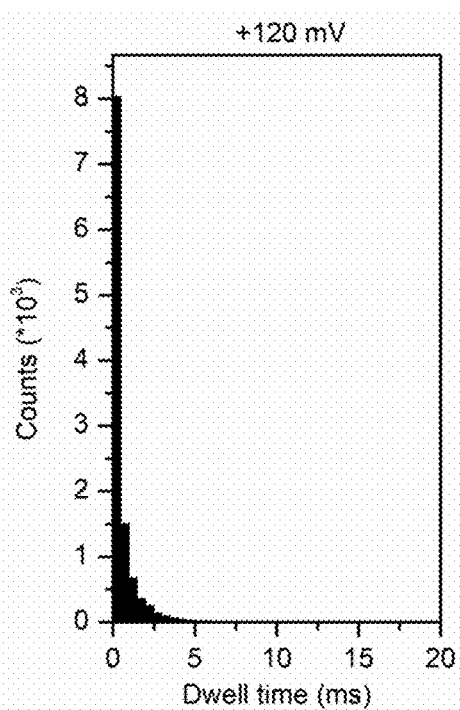
FIG. 25: Blockade of about 78% and translocation time of about 0.5 ms are induced by ssDNA pass through pores of mutant E1 (306-605, K421L, H323W).
Figure 26:
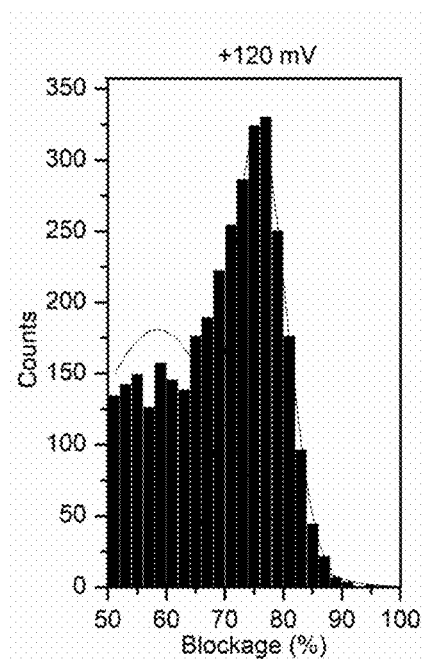
FIG. 26: The unwinding current signal is induced by the dsDNA with single-arm transport the unwinding of a mutant E1 (306-605, K421L, H323W) on an artificial lipid membrane in PBS buffer. Three steps appear in the signal, corresponding to the single-arm of the double-stranded inlet blockage, unwinding process, single-stranded plugging and opening state. The total unwinding time is 270 ms.

E1 protein mutant is translocated by ssDNA/ssRNA using the same conductance conditions and single stranded nucleic acid. Under the conductance condition of 1M KCl and 10 mM Hepes (pH7.5), applying the bias voltage of 120 mv, it finds that the blocking rate of ssDNA translocation is close to 78%, and the translocation time is close to 0.5 ms (as shown in FIGS. 26 and 25), which approximates to the data of WT-E1 (306-605).

Embodiment Six, Blockage Experiment of dsDNA Inside E1

The double-stranded DNA (dsDNA) obtained from BamH1 enzyme is added to the cis-chamber, and the translocation buffer is 10 mM HEPES/1M KCl with ssDNA. The transfer signals are detected at 50 mv, 70 mv, 120 mv and 150 mv voltages respectively, and no dsDNA translocation is observed.

Embodiment Seven, Verification Experiment of E1 Nucleic Acid Translocation

Figure 11:
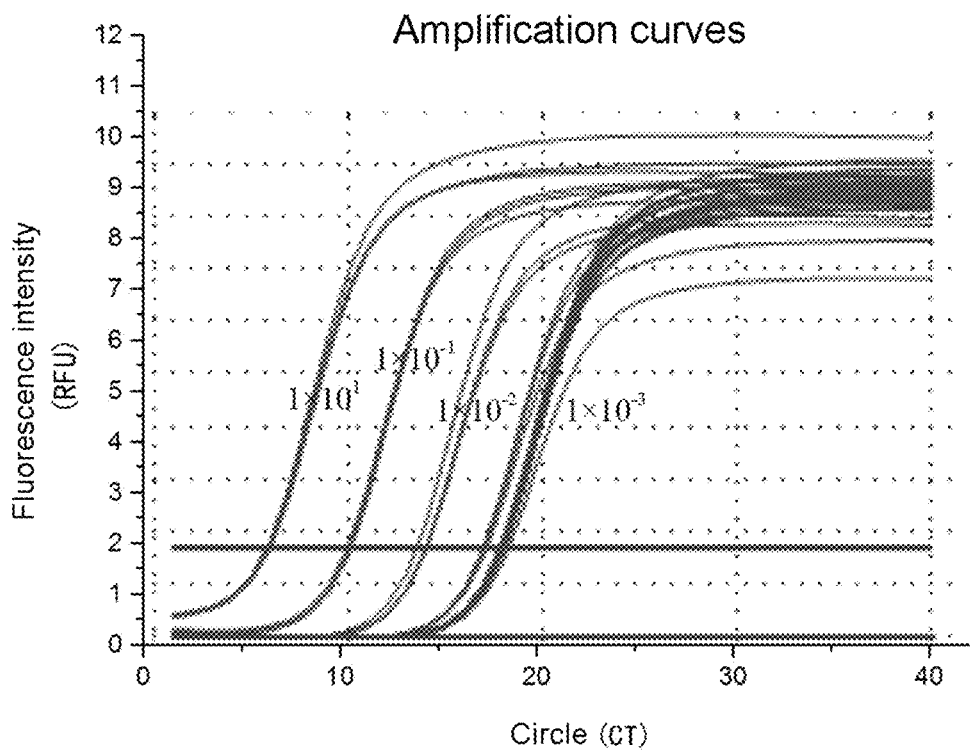
FIG. 11: Two complementary ssDNA synthesized at a certain concentration of 80 nt are diluted 10 times into 10 concentration gradients, and four ssDNA of adjacent concentrations are selected to complete the Q-PCR quantitative analysis experiment.
Figure 12:
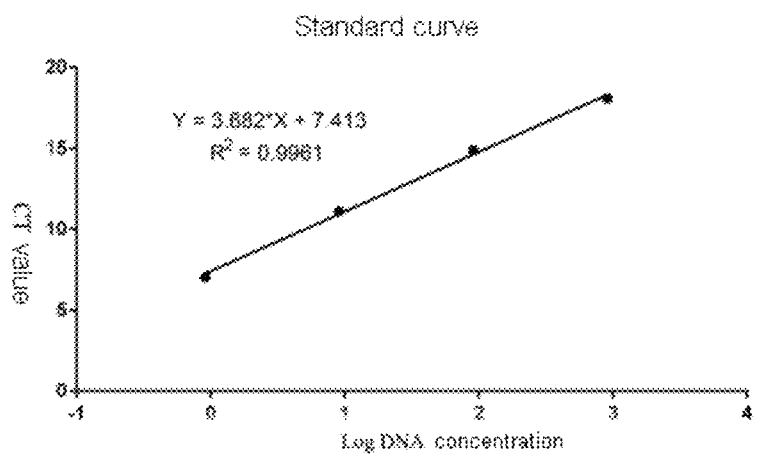
FIG. 12: Preparation of a standard curve is performed using CT values obtained from Q-PCR and constant concentrations of ssDNA as described above.

Q-PCR is used to make the standard curve of nucleic acid amplification: dsDNA is prepared from annealing two ssDNA (80nt) and identified with 2% agarose gel, and extracted from gel. The concentration of dsDNA extracted from gel is determined by Qubit®3.0 (Thermo fisher scientific Co. Ltd, America) (This method is better than ultraviolet spectrophotometer in accuracy and precision); The resulting dsDNA of known concentration is diluted into 10 of 10-time concentration gradients, and then using Q-PCR (Premix SYBR-Takara Co. Ltd, Japan) to make the standard curve for the ct value of dsDNA concentration, so as to obtain the standard correlation (as shown in FIGS. 11-12, Ct value has a good repeatability under each concentration gradient, and $R^2=0.99+$. Therefore, this standard correlation can be used as a basis for the calculation of subsequent ssDNA translocation experiments.)

Quantitative analysis of ssDNA through pore by Q-PCR, as mentioned above, after E1 protein embedded into the membrane in cis-chamber, adding 50 nM 80 nt-DNA (the first method), or premixing 25 nM 48 nt-DNA into conductance buffers at both side chambers (the second method). As a negative control, 50 nM 80nt-DNA is added to cis-chamber without E1 protein, or the equivalent amount of 25 nM 80nt-DNA is added to both side chambers. Applying a voltage of −70 mV to both sides of the membrane and collecting two-chambers' conductance buffer for Q-PCR quantitative analysis after 10 min, 20 min, 40 min, 60 min and 90 min, respectively.

All nucleic acids involved in translocation experiments are described below: (purchased from Takara, Co. Ltd, Japan)

48 nt-DNA sequence is shown in SEQ ID No. 16:
3'-TTT TTT TTT AAA AAA TTT TTT GGG GGG TTT

TTT CCC CCC TTT TTT TTT-5'.

-continued

Sequences of 44 nt-DNA and 44 nt-DNA 1 are shown
in SEQ ID No. 17 and SEQ ID No. 18, respectively:

(SEQ ID No. 17)
5'-AGC TCC ACC CCT CCT GGT AAC CAG TTT TTT TTT

TTT TTT TTT TT-3'.

(SEQ ID No. 18)
5'-TTT TTT TTT TTT TTT TTT TT CTG GTT ACC AGG AGG

GGT GGA GCT-3'.

24 nt-DNA sequence is shown in SEQ ID No. 19:

5'-CTG GTT ACC AGG AGG GGT GGA GCT-3'.

Labeled nucleic acid chain and labeled nucleic acid chain 1 are described as SEQ ID No. 20 and SEQ ID No. 21:

(SEQ ID No. 20)
5'-CCTACGCCACCAGCTCCGTAGG-3' (5'-Cy5, 3'-BHQ2).

(SEQ ID No. 21)
5'-CCTACGGAGCTGGTGGCGTAGGTTTTTTTTTTTTTTTTTTTT-3'.

The sequences of dsDNA and dsDNA1 with dspacer (dspacer is a nucleotide having only a phosphate skeleton and no bases, therefor its spatial structure is smaller than normal nucleotides) are shown in SEQ ID No. 22 (three dspacer are inserted between the eleventh and twelfth bits) (the detail sequence is 5'-TTTTTTTTTTT XXXTTTTTTTTTT-3', and X represents dspacer) and SEQ ID No. 23:

(SEQ ID No. 22)
5'-TTTTTTTTTTTTTTTTTTTTTT-3'.

(SEQ ID No. 23)
5'-AAAAAAAAAAAAAAAAAAAA-3'.

The sequence of nucleic acid used in quantitative translocation analysis by Q-PCR are shown in SEQ ID No. 24 and SEQ ID No. 25:

(SEQ ID No. 24)
5'-CAG GCA GAG GAC AGA TAT TTG TAC TTG CAT AGT

CGG GTG CAA ACC TTT CGC TTT GAG CAG CCA TGC ACA

GAT GAA TCG GGT TTT TTT TTT TTT TTT TTTT.

(SEQ ID No. 25)
5'-CCC GAT TCA TCT GTG CAT GGC TGC TCA AAG CGA

AAG GTT TGC ACC CGA CTA TGC AAG TAC AAA TAT CTG

TCC TCT GCC TG.

The two primers (primer 1 and primer 2) used for quantitative translocation by Q-PCR are shown in SEQ ID no.26 and SEQ ID no.27, respectively:

(SEQ ID No. 26)
5'-CAG GCA GAG GAC AGA TAT TT.

(SEQ ID No. 27)
5'-CCC GAT TCA TCT GTG CAT GG.

Figure 13:
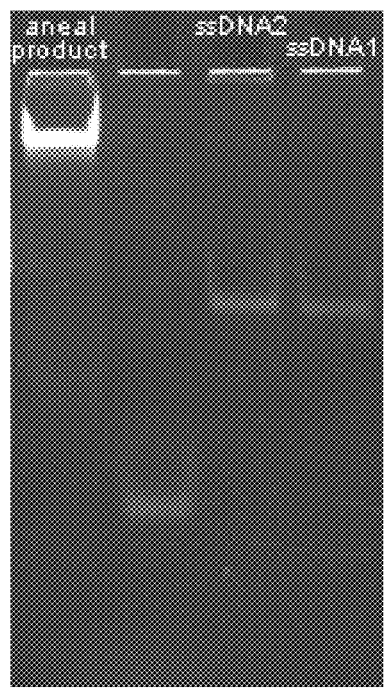
FIG. 13: All double-stranded nucleic acids in this invention are obtained by this method: double-strand annealing is performed on a PCR machine, the denaturation temperature is 95° C., the time is two minutes, and the gradient process is set in the cooling process (about 1 degree per minute). It takes 1 hour and 20 minutes. The obtained nucleic acid product is analyzed by polyacrylamide gel electrophoresis.

The annealing procedure of dsDNA is performed at PCR equipment, the annealing temperature is 95° C., and the annealing time is set up to 2 min; then the process of cooling is set up to gradient (almost 1° C./min), which lasts 1 h and 20 min. Lastly, the nucleic acid product is determined by agarose gel (as shown in FIG. 13).

In this invention, dsDNA is acquired from circular plasmid Hag-C1 digested by BamH1, and it is purified by QIAGEN DNA purification kit the product 3800 bp dsDNA was conducted by QIAGEN DNA purification kit (QIAGEN, Co. Ltd, Germany).

Embodiment Eight, Unwinding Experiment of E1 In Vitro

The invention using E1 (306-577) to verify the helical activity of ds DNA of the protein hexamer in vitro.

The buffer solution in helicase experiment is 20 mM HEPES (pH 7.5), 0.7 mg/ml BSA, 5% Glycerol, 5 mM $MgCl_2$, 3 mM DTT; And the reaction is initiated by adding 2 mM ATP; the substrate dsDNA in this trial is 22 bp labeled with 5'-fluor and 3'-quencher at the terminals of DNA which could form hairpin spontaneously.

In vitro, dsDNA ends flat cannot be directly unwind by this helicase due to the lack of other protein components contained in the virus itself to assist in DNA replication.

Synthesized dsDNA with a single stranded arm is used in the unwinding experiment in vitro and unwinding experiment on membrane mentioned later. E1 protein unwinding starts with the single-arm nucleic acid strand entering the pore. In the process of unwinding, excitation wavelength is 643 nm and emission wavelength is 667 nm, Multifunctional fluorescence microplate reader (Bio-Tek, Co. Ltd, America) is used to continuously monitor the fluorescence of the substrate (5 nM nucleic acid substrate) in the reaction system to visually observe the unwinding process. When dsDNA is unwound, one of the ssDNA terminal forms spontaneously hairpin structure, and fluorescence tag could be quenched by quencher tag.

Figure 14:
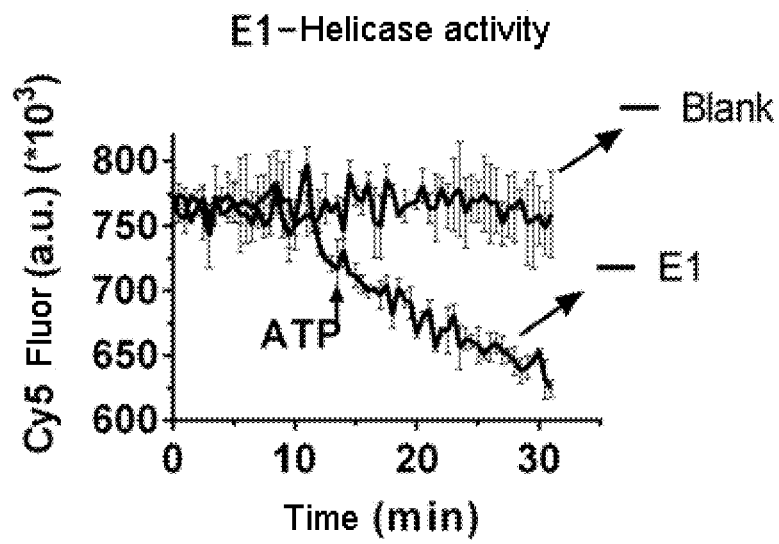
FIG. 14: Detection of the helicase activity of E1-1 (306-577) by quenching the fluorophore Cy5 with the fluorescence quenching group BHQ2 at both ends of one strand of dsDNA.

The result demonstrates that, E1-2 has helicase activity in vitro, double-stranded nucleic acids can be unwound in the presence of ATP, as shown in FIG. 14.

Embodiment Nine, Unwinding Experiments of E1 and its Mutant on the Artificial Lipid Membrane After verifying the helicase activity of E1 in vitro, unwinding experiments on the artificial lipid membrane is planned: after insertion of E1 into the BLM, dsDNA could not be translocation through the E1 protein at the room temperature (21° C.) in the absence of ATP and $Mg^{2+}$ because of the diameter of double-stranded DNA is larger than the diameter of E1 protein pore (as mentioned above).

Figure 15:
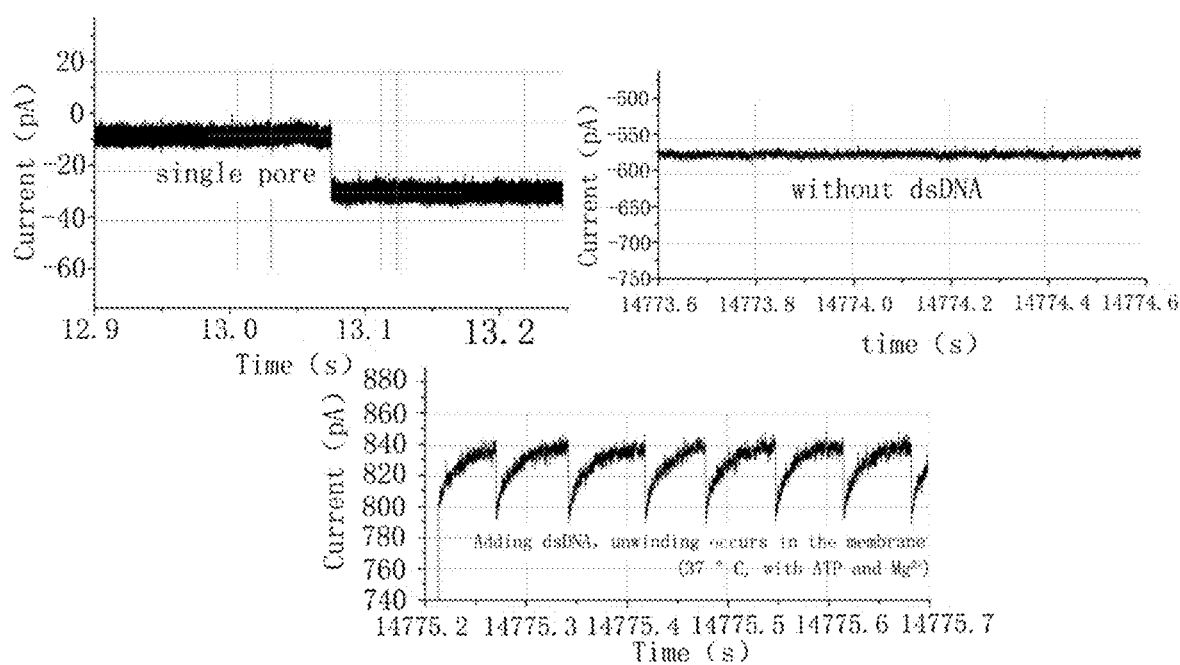
FIG. 15: By controlling the appropriate system environment, including ATP concentration, $Mg^{2+}$ concentration, system temperature, etc., we observed the phenomenon of double-stranded DNA transport through E1 at the molecular level.

However, by controlling the appropriate system environment, including the concentration of ATP, $Mg^{2+}$ concentrations, and system temperature, dsDNA translocation through E1 is observed at the molecular level (as shown in FIG. 15). As a comparison, we chose another MspA without helicase activity (the diameter of its pore is similar to that of E1 and smaller than that of double-stranded DNA) to transfer double-stranded DNA, and the results show that under the conditions of non-unwinding system (ATP-free, $Mg^{2+}$) and the same temperature, ATP concentration and $Mg^{2+}$ concentration as E1-2, double-stranded DNA cannot be transported through MspA porin.

Because low salt concentration is needed in E1 helicase activity determination experiments, PBS is chosen to conduct the unwinding on the artificial lipid membrane; in this buffer solution, the conductance of E1-2 is about 0.2±0.02 nS.

The scheme of this experiment is described below: After BLM is formed in PBS conductance buffer, E1-2 steady inserts into BLM (as described above); then dsDNA (final concentration of 12.5 nM) is added into cis-chamber and heats up the conductance buffer with a heating plate to 37° C.; then ATP (final concentration of 5 mM) and $Mg^{2+}$ (final concentration of 5 mM) are added into the conductance buffer.

Figure 16:
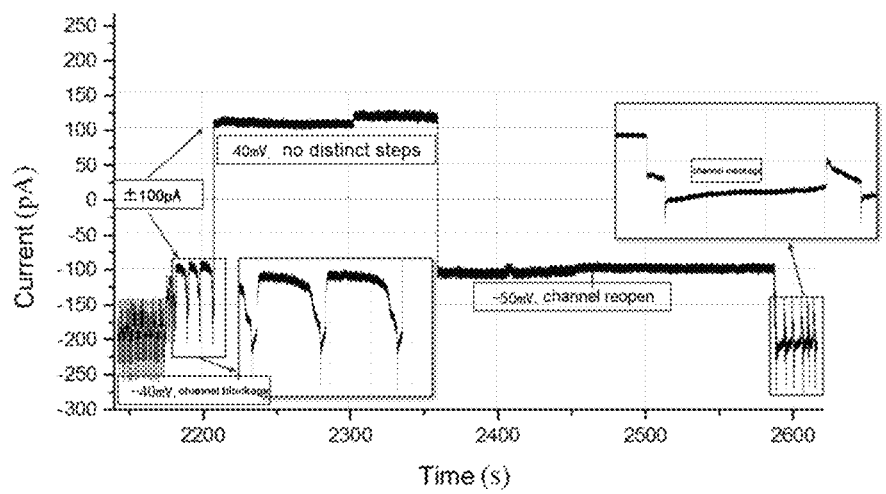
FIG. 16: We found a large number of unwinding dsDNA transport phenomena at −40 mV. We reversed the voltage to +40 mV in the double-chain blockage state during the unwinding process. It was found that the phenomenon of pore blockage continued, and when the voltage returned to −50 mV, the unwinding phenomenon reappears and the unwinding restarts from the blocked state.

The result displays that, with ATP hydrolysis, dsDNA is unwound as ssDNA by E1-2 embedded in the BLM and is translocated from cis- to trans-side. Under −40 mV, amounts of dsDNA unwinding phenomenon are observed and pores will keep blockage as the voltage is reversed to +40 mV. However, with voltage changing from +40 mV to −50 mV, the unwinding occurs again and it restarts from the blocked state (as shown in FIG. 16).

dsDNA with Different Lengths Unwinding on Membrane:

Moreover, the invention explores the unwinding phenomenon of dsDNA with different lengths on the artificial lipid membrane.

Figure 17:
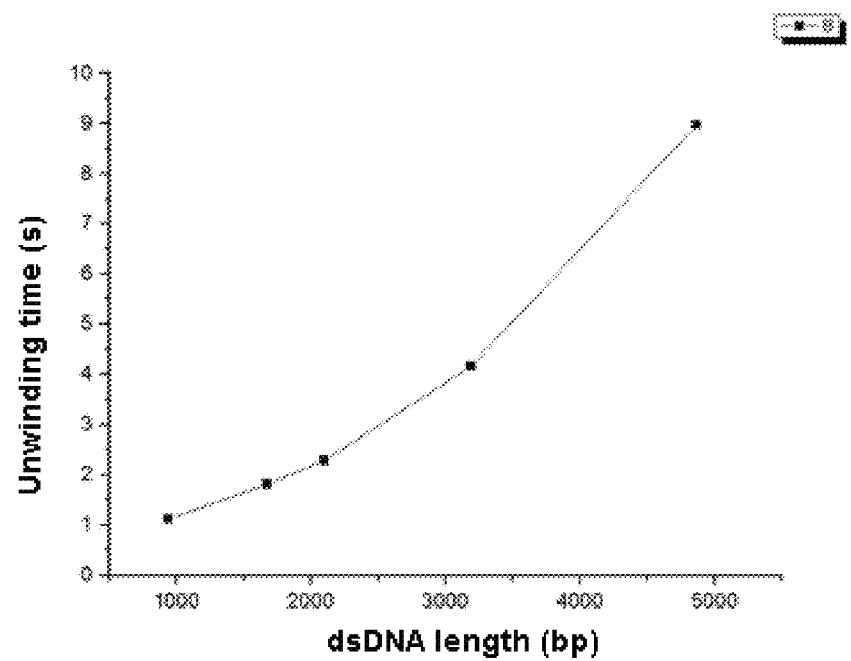
FIG. 17: E1-2 (306-605) also increases the unwinding time as the length of the double strand increases: at a voltage of −100 mV, I pore=−400 pA N=20, when the dsDNA chain length is less than 2000 bp, the melting speed is close to uniform. When the chain length of dsDNA is longer, we find that the untwisting activity of E1-2 is decreased. When the chain length is close to 5000 bp, the unwinding time reaches 9 s.
Figure 18:
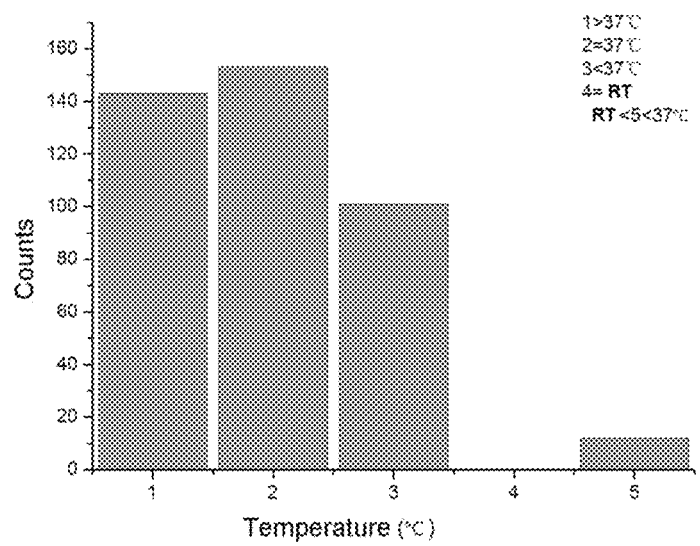
FIG. 18: The experiments are carried out at room temperature (21° C.), 37° C., lower than 37° C. and higher than 37° C. It is found that with the increase of temperature, the number of occurrences of unwinding increases obviously proportionally. When the temperature is higher than 37° C., the number of unwinding occurrence decreases again.
Figure 19:
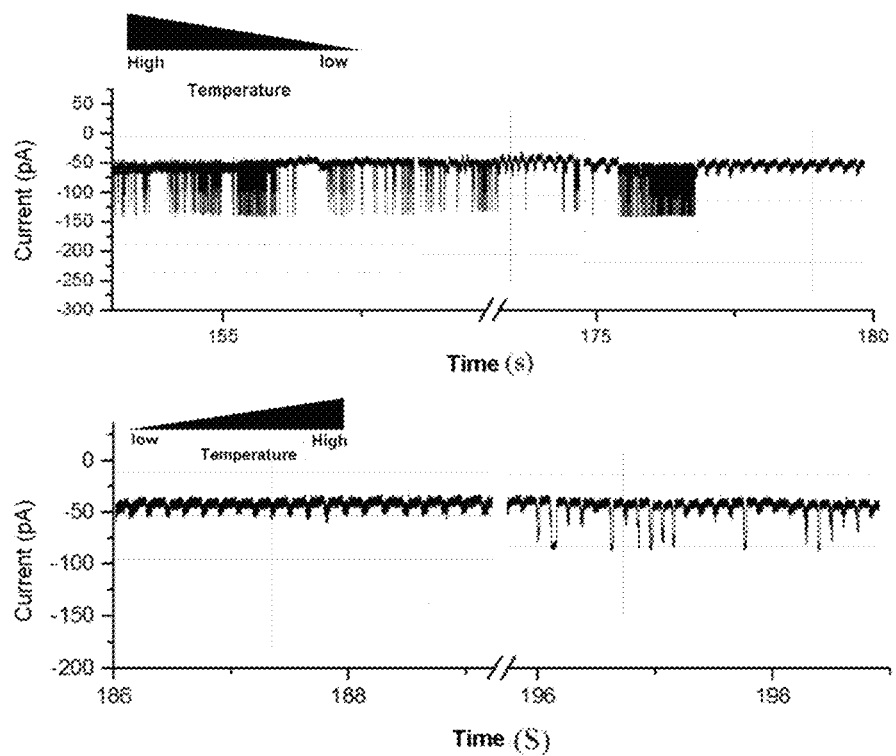
FIG. 19: As the temperature of the system decreases, it can be seen that the unwinding on the membrane is gradually reduced. When the temperature is returned from low temperature to high temperature, it is found that the unwinding increases.

Recombinant plasmid PET-28b+MspA is digested with XhoI and EcoO109I to five different lengths of fragments; Since both enzymes can digests linear double strands with sticky ends, dsDNA has an extended single arm (the length is 5 bp, for the reasons mentioned above), so dsDNA with 5 different lengths is used to explore the influence of different strand's lengths on unwinding on the membrane, and the experimental process is the same as above The results show that, under the same other conditions, with the increase of strand's length, the unwinding time of E1-2 also increases proportionally. As shown in FIG. 17, under −100 mV, $I_{pore}$=−400 pA (N=20), and when the length of dsDNA is less than 2000 bp, the velocity of unwinding is relatively constant, but, with the length of dsDNA getting longer, it is found that the unwinding activity of E1-2 decreases, and when the length is close to 5000 bp, the unwinding time reaches 9 s.

dsDNA Unwinding on Membrane at Different Temperatures:

On the other hand, this invention attempts to observe the unwinding phenomenon of dsDNA on the membrane under same conditions except different temperatures. The experiments of 24 bp nucleic acid strand mentioned above are conducted at gradient temperatures, respectively, room temperature (21° C.), lower than 35° C., 35° C. −37° C., and higher than 37° C., The results show that the frequency of unwinding increases proportionally with the increase of temperature, but when the temperature is higher than 37° C., the unwinding begins to decrease, which is consistent with the characteristics of E1-2 as a viral helicase (as shown in FIGS. 18 and 19).

dsDNA Unwinding on Membrane at Different Transmembrane Voltages:

This invention also determines the time required for E1-2 unwinding the same dsDNA substrate at different transmembrane voltages, and the experimental process is the same as above mentioned.

Figure 20:
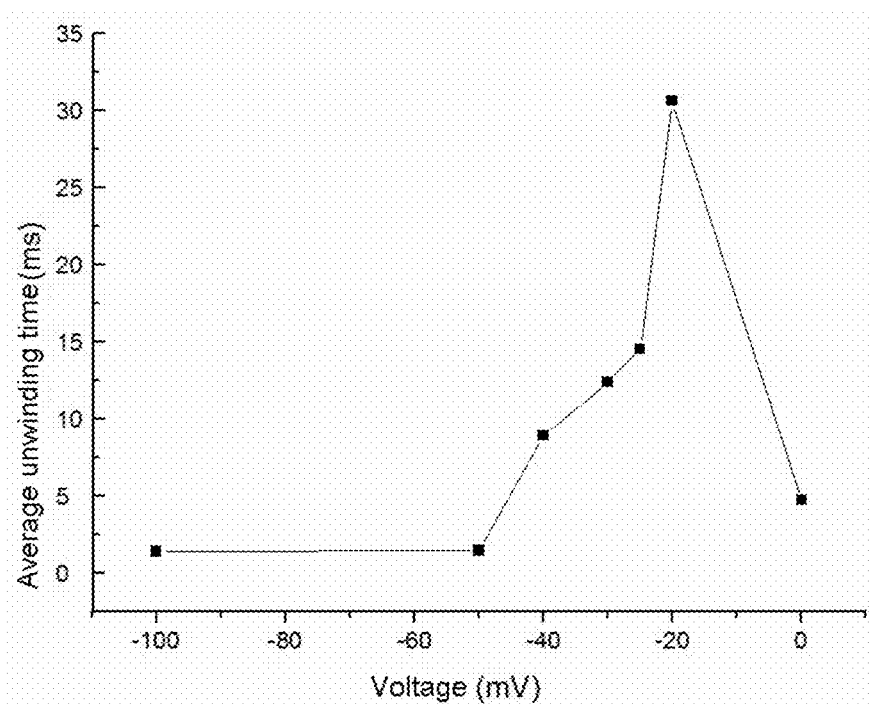
FIG. 20: For the same double-stranded DNA substrate, we found that it takes about 3 s to melt at −100 mV. When the voltage becomes −20 mV, the melting time is nearly 30 s. According to the fitting curve direction, the voltage drive chain moves in the same direction as the unwinding direction of E1-2.

The experimental results show that with nucleic acid substrate mixing into the cis-chamber, the unwinding time is extended accordingly when the absolute voltage value is gradually reduced at negative voltage, and a non-linear function is fitted with the voltage gradient and unwinding time. The resulting curve is oriented towards the axis, which shows and proves that in addition to the driving force of voltage, E1-2 is also actively unwinding, and the direction of the two forces is the same. As shown in FIG. 20, for the same dsDNA substrate, it takes about 3 s for unwinding at a voltage of −100 mV, while at a voltage of −20 mV, the unwinding time increases to nearly 30 s. According to the direction of the fitting curve, the direction of voltage-driven unwinding is the same as the direction of E1-2 unwinding. Since E1 is a mushroom structure and a single strand enters the protein pore from the opening of N-terminal during DNA replication, thus it can be known that the N-terminal opening of the protein in this state towards the negative electrode of cis-chamber.

The Unwinding of Special Nucleic Acid Substrate on Membrane:

This invention also designs another special nucleic acid substrate with three dspacers (without bases) in one strand of dsDNA, which has single arm and consists of A and T. The unwinding experiment is conducted with this special nucleic acid substrate.

It founds that in normal unwinding signal, small steps with a size of 20-30 pA appears at specific locations. And the specific locations of small step signals are consistent with those of the dspacers in nucleic acid.

Verifying E1 Unwinding on Membrane (Depending on the Function of $Mg^{2+}$ and ATP):

To verify the unwinding of E1-2 on membrane, excess EDTA which chelated with $Mg^{2+}$ is applied to inactivate the helicase. The experimental process is the same as the above mentioned. In the process of unwinding, excess of EDTA chelator is added to the reaction system.

The results show that with the increase of EDTA, the unwinding activity is gradually inhibited, and the maximum inhibition efficiency reaches to more than 80%. When excess $Mg^{2+}$ is added to the reaction system, it is clearly observed that the unwinding reappears, recovering to maximum efficiency by ½ or more.

At the same time, when ATPαS, another analog of ATP, is used to competitively replace ATP in the unwinding system, it is found that ATPαS could not hydrolyze to supply energy like ATP, the unwinding activity on membrane is significantly inhibited. Because this inhibition is not as reversible as EDTA chelating $Mg^{2+}$, when excess ATPαS is added, the unwinding activity on membrane gradually disappears.

Figure 27:
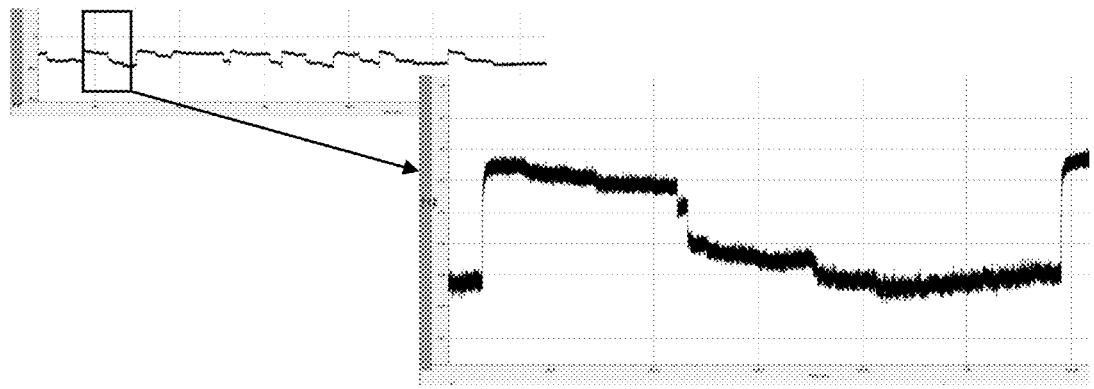
FIG. 27: A representative unwinding current trace induced by atypical dsDNA transport the unwinding action of mutant action of mutant E1 (306-605, K421L, H323W).
Figure 28:
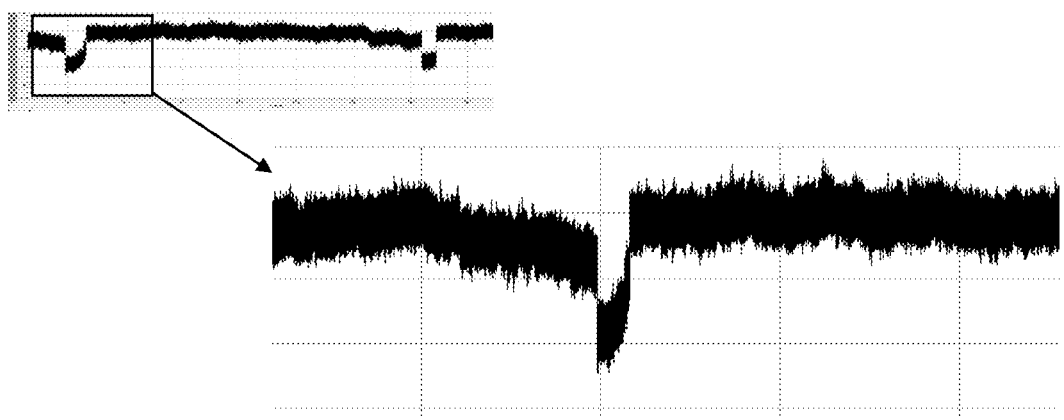
FIG. 28: Another typical unwinding current trace induced by atypical dsDNA transport the unwinding action of mutant E1 (306-605, K421L, H323W).

Studying the unwinding of E1 mutants on artificial lipid membranes with the same experimental methods and conditions, it is found that the translocation of mutant of E1 protein is initiated by 2 mM ATP. The unwinding signal similar to WT-E1 (306-605) is observed at a bias voltage of −100 mV, as shown in FIGS. 27, 28.

The above results show that, for the first time, a cyclic hexameric helicase of bovine papilloma virus has been successfully engineered into a protein nanopore, which is embedded in lipid bilayer membrane and polymer membrane. The Nanopore can stably stay on lipid bilayer without gating at high voltage. And it still keeps the characteristics of a helicase on artificial lipid membranes, such as temperature specificity, and competitive inhibition by ATP analogues. This nanopore can passively translocate single-stranded RNA as well as single-stranded DNA on membrane. And dsDNA with a single arm can be unwound on membrane using energy supplied by ATP hydrolysis, with the unwinding time positively proportional to the length of substrate.

The above experiments show that this invention innovatively discovers two proteins E1-1 (306-577) and E1-2 (306-605), wherein the former can be used as a new simple membrane containing conductive pore, and it can insert into lipids bilayer stably and translocation nucleic acid, the latter further has dual effects of nanopore and helicase. This invention constructs a sensing system combining the characteristics of nanopore and helicase, which replaces the existing sensing method requiring helicase a coupling nanopore, and has a good application prospect.

Further, this invention also creatively studies the mutant of E1-2 protein, obtains mutants of E1-2. It is found that the nanopore constructed by mutated monomer is more likely to capture nucleic acids and other negatively charged small molecules than the wild type protein. In addition, the mutated protein shows an increase in current range, which makes the inner cavity of the pore narrower than that of the wild type, so that the current detection of the pore is more extensive and sensitive.

The invention claimed is:

1. A protein having an ability to form a multimeric protein pore having helicase activity, wherein the protein comprises the amino acid sequence of SEQ ID NO: 7.

2. A multimeric protein, which comprises two or more proteins according to claim 1.

3. The multimeric protein according to claim 2, which comprises 4 to 8 of the proteins.

4. The multimeric protein according to claim 3, which comprises 6 of the proteins.

5. The multimeric protein according to claim 2, wherein the multimeric protein is a homomultimer or a heteromultimer.

6. A membrane comprising:
   a) a membrane layer; and
   b) the multimeric protein of claim 2,
   wherein the multimeric protein is embedded in the membrane layer to form a conductive channel, which is electrically conductive when a transmembrane potential is applied.

7. A method of making a membrane comprising a conductive channel, the method comprising the steps of:
   a) preparing dried amphiphilic lipids; and
   b) resuspending the dried amphiphilic lipids in a solution comprising aqueous solvent, penetrating agent and proteins according to claim 1 under conditions and sufficient time to form a membrane comprising the conductive channel.

8. A single-molecule sensor or kit comprising the protein according to claim 1.

9. A polynucleotide comprising a nucleotide sequence encoding the protein according to claim 1.

10. A vector comprising the polynucleotide of claim 9.

11. A host cell comprising the vector of claim 10.

12. An artificial membrane comprising:
   a) a membrane layer; and
   b) the protein according to claim 1,
   wherein the protein is embedded in the membrane layer to form a conductive channel, which is electrically conductive when a bias voltage is applied.

13. A single-molecule sensor or kit, comprising the artificial membrane according to claim 12.

* * * * *